(12) United States Patent
Yonak et al.

(10) Patent No.: US 8,945,539 B1
(45) Date of Patent: *Feb. 3, 2015

(54) ENZYME AND PREBIOTIC COMBINATIONS FOR ENHANCING PROBIOTIC EFFICACY

(71) Applicant: Master Supplements, Inc., Victoria, MN (US)

(72) Inventors: Sonja L. Yonak, Prior Lake, MN (US); Randolph S. Porubcan, Victoria, MN (US)

(73) Assignee: Master Supplements, Inc., Victoria, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/074,033

(22) Filed: Nov. 7, 2013

(51) Int. Cl.
- *A61K 38/43* (2006.01)
- *A01N 63/00* (2006.01)
- *A61K 31/702* (2006.01)
- *A61K 38/47* (2006.01)

(52) U.S. Cl.
CPC .............. *A61K 38/47* (2013.01); *A61K 35/747* (2013.01); *A61K 35/745* (2013.01); *A61K 31/702* (2013.01)
USPC ......................................... 424/94.1; 424/93.1

(58) Field of Classification Search
USPC ................................................ 424/94.1, 93.1
See application file for complete search history.

(56) References Cited

U.S. PATENT DOCUMENTS

| | | | | |
|---|---|---|---|---|
| 8,066,986 | B2 * | 11/2011 | Porubcan | 424/93.3 |
| 8,568,712 | B2 * | 10/2013 | Porubcan et al. | 424/94.1 |
| 2012/0207831 | A1 * | 8/2012 | Stella et al. | 424/465 |

FOREIGN PATENT DOCUMENTS

WO  WO 2005/032591  *  4/2005  ............. A61K 47/00

* cited by examiner

*Primary Examiner* — Karen Cochrane Carlson
*Assistant Examiner* — Natalie Moss
(74) *Attorney, Agent, or Firm* — Eric P. Mirabel

(57) ABSTRACT

This disclosure relates to enhancing growth and/or activity of lactobacilli using a prebiotic formulation which includes iso-malto oligosaccharides and α-galactosidase; and to enhancing growth and/or activity of bifidobacteria using a prebiotic formulation which includes iso-malto oligosaccharides and β-glucanase. Other combinations of fibers and enzymes are described below which also stimulate growth and activity of lactobacilli or bifidobacteria. These combinations of enzymes and prebiotics can be taken separately or added to foods, including desserts.

29 Claims, 28 Drawing Sheets

Figs. 1A, 1B: Growth & Activity of BL-04 (*Bifidobacterium lactis*) in MRS broth ("Control (scratch)") and MRS broth with glucose removed (hereinafter "No-G-Broth") and VitaFiber™ substituted for it.

Figs. 2A, 2B: Growth and activity of NCFM (*Lactobacillus acidophilus*) in MRS broth ("Control (scratch)") and in No-G-Broth with VitaFiber™ substituted for glucose.

Figs. 3A, 3B: Growth and activity of BL-04 (*B.fidobacterium lactis*) in No-G-Broth with VitaFiber™ substituted for glucose, and where VitaFiber™ was pre-digested with cellulase.

Figs. 4A, 4B: Growth and activity of NCFM (*Lactobacillus acidophilus*) in No-G-Broth with VitaFiber™ substituted for glucose, and where VitaFiber™ was pre-digested with pectinase.

Figs. 5A, 5B: Growth and activity of BL-04 (*B.fidobacterium lactis*) in No-G-Broth with VitaFiber™ substituted for glucose, and where VitaFiber™ was pre-digested with either β-glucanase or α-galactosidase.

Figs. 6A, 6B: Growth and activity of NCFM (*Lactobacillus acidophilus*) in No-G-Broth with VitaFiber™ substituted for glucose, and where VitaFiber™ was pre-digested with either β-glucanase or α-galactosidase.

Figs. 7A, 7B: growth and activity of BL-04 (B.fidobacterium lactis) in No-G-Broth with partially hydrolyzed guar gum substituted for glucose, and where PHGG was pre-digested with either β-glucanase or α-galactosidase.

Figs. 8A, 8B: growth and activity of NCFM (*Lactobacillus acidophilus*) in No-G-Broth with partially hydrolyzed guar gum substituted for glucose, and where PHGG was pre-digested with either β-glucanase or α-galactosidase.

Figs. 9A, 9B: growth and activity of LP-115 (*Lactobacillus plantarum*) in No-G-Broth with VitaFiber™ substituted for glucose, and where VitaFiber™ was pre-digested with either pectinase or a 50:50 mix of α-galactosidase plus pectinase.

Figs. 10A, 10B: growth and activity of NCFM (*Lactobacillus acidophilus*) where VitaFiber™ was pre-digested with α-galactosidase before the remaining No-G-Broth ingredients (except polysorbate 80) were added along with added LactoStim™, or pre-digested with α-galactosidase plus pectinase.

Figs. 11A, 11B; growth and activity of BL-04 (*B.fidobacterium lactis*) where VitaFiber™ was pre-digested with β-glucanase then grown in No-G-Broth without polysorbate 80 but with LactoStim™, and where VitaFiber™ was pre-digested with β-glucanase and cellulose then grown in No-G-Broth.

Figs. 12A, 12B; growth and activity of BL-04 (*Bifidobacterium lactis*) in No-G-Broth with inulin substituted for glucose, and where inulin was pre-digested with β-glucanase then grown in No-G-Broth.

Figs. 13A; 13B; growth and activity of NCFM (*Lactobacillus acidophilus*) in No-G-Broth with inulin substituted for glucose, and where inulin was pre-digested with α-galactosidase then grown in No-G-Broth without polysorbate 80 but with LactoStim™.

Figs. 14A; 14B; growth and activity of BL-04 (*B.fidobacterium lactis*) in No-G-Broth with VitaFiber™ substituted for glucose, and where VitaFiber™ was pre-digested with one of two different concentrations of β-glucanase.

Figs. 15A; 15B: growth and activity of NCFM (*Lactobacillus acidophilus*) in No-G-Broth with VitaFiber™ substituted for glucose, and where VitaFiber™ was pre-digested with one of: (i) α-galactosidase; (ii) a first, lower concentration of α-galactosidase and β-glucanase; and (iii) a higher concentration of α-galactosidase and β-glucanase.

Figs. 16A; 16B: growth and activity of BL-04 and NCFM (i) in MRS broth, (ii) in No-G-Broth with VitaFiber™ substituted for glucose, (ii) where VitaFiber™ was pre-digested with a 1:3 blend of β-glucanase and α-galactosidase before (a) adding the other ingredients in No-G-Broth, (b) adding LactoStim™ and the other ingredients in No-G-Broth but not polysorbate 80.

Figs. 17A; 17B: growth and activity of *Latobacillus salivarius* (LS-33) where VitaFiber™ was pre-digested with one of: (i) α-galatosidase; (ii) β-glucanase; and (iii) a 1:3 blend of β-glucanase and α-galatosidase; before adding LactoStim™ and the other ingredients in No-G-Broth but not polysorbate 80.

Figs. 18A; 18B: growth and activity of *Lactobacillus paracasei* (LPC-37) where VitaFiber™ was pre-digested with one of: (i) α-galatosidase; (ii) β-glucanase; and (iii) a 1:3 blend of β-glucanase and α-galatosidase, before adding LactoStim™ and the other ingredients in No-G-Broth but not polysorbate 80.

Figs. 19A; 19B: growth and activity of *Lactobacillus plantarum* (LP-115) where VitaFiber™ was pre-digested with one of: (i) α-galatosidase; (ii) β-glucanase; and (iii) a 1:3 blend of β-glucanase and α-galatosidase before adding LactoStim™ and the other ingredients in No-G-Broth but not polysorbate 80.

Figs. 20A; 20B: growth and activity of *Lactobacillus rhamnosus* (Lr-32) where VitaFiber™ was pre-digested with one of: (i) α-galatosidase; (ii) β-glucanase; and (iii) a 1:3 blend of β-glucanase and α-galatosidase before adding LactoStim™ and the other ingredients in No-G-Broth but not polysorbate 80.

Figs. 21A; 21B: growth and activity of *Bifidobacterium lactis* (Bi-07) where VitaFiber™ was pre-digested with one of: (i) α-galatosidase; (ii) β-glucanase; and (iii) a 1:3 blend of β-glucanase and α-galatosidase, before adding LactoStim™ and the other ingredients in No-G-Broth but not polysorbate 80.

Figs. 22A; 22B: growth and activity of *Lactobacillus rhamnosus* (LR-32) with Wheat Dextrin in No-G-Broth, and where Wheat Dextrin was pre-digested with α-galatosidase before adding the other ingredients in No-G-Broth.

Figs. 23A; 23B; growth and activity of *Lactobacillus salivarius* (LS-33) with Wheat Dextrin in No-G-Broth, and where Wheat Dextrin was pre-digested with α-galatosidase before adding the other ingredients in No-G-Broth.

Figs. 24A; 24B; growth and activity of *Lactobacillus acidophilus* (NCFM) with Wheat Dextrin in No-G-Broth, and where Wheat Dextrin was pre-digested with α-galatosidase before adding the other ingredients in No-G-Broth.

Figs. 25A; 25B; growth and activity of *Bifidobacterium lactis* (BL-04) with Wheat Dextrin in No-G-Broth, and where Wheat Dextrin was pre-digested with β-Glucanase before adding the other ingredients in No-G-Broth.

Figs. 26A; 26B; growth and activity of *Bifidobacterium lactis* (Bi-07) with Wheat Dextrin in No-G-Broth, and where Wheat Dextrin was pre-digested with β-Glucanase before adding the other ingredients in No-G-Broth.

Figs. 27A; 27B; growth and activity of *B.fidobacterium breve* (BB-03) with Wheat Dextrin in No-G-Broth, and where Wheat Dextrin was pre-digested with β-Glucanase before adding the other ingredients in No-G-Broth.

Figs. 28A; 28B; growth and activity of *Lactobacillus plantarum* (LP-115) with Wheat Dextrin in No-G-Broth, and where Wheat Dextrin was pre-digested with either pectinase or α-galactosidase before adding the other ingredients in No-G-Broth.

ENZYME AND PREBIOTIC COMBINATIONS FOR ENHANCING PROBIOTIC EFFICACY

FIELD OF THE APPLICATION

The field is enzymes and prebiotics for enhancing probiotic efficacy.

BACKGROUND

Lactic acid producing bacteria that are capable of improving or maintaining intestinal health and function, including reducing constipation (primarily from the *Lactobacillus* and *Bifidobacterium* genera) are termed probiotic bacteria. Dietary supplements with probiotic bacteria as the active ingredient currently enjoy sales of over $700 million annually, and the market growth is approaching 30% annually. The other piece of the probiotic market is probiotic foods, especially yogurt and desserts. This segment of the market is over $1 Billion annually.

The reported health benefits of probiotics include supporting the immune system (inhibiting allergic response and neoplastic growth), treating inflammatory bowel disease, offsetting lactose intolerance, and reducing cholesterol. They are also useful for repopulating the gut after antibiotic therapy. Probiotic growth in the intestinal tract, following ingestion, depends to a large extent on the nutrients present in the patient's diet. Typical human diets are not well suited for probiotics and, given the abundance of and competition from many less fastidious digestive tract bacteria (including pathogenic strains such as clostridium, rotaviruses, pathogenic *E. coli* and *Helicobacter pylori*) it can be difficult for probiotics to effectively multiply in vivo. To help correct this problem, manufacturers of probiotic dietary supplements often include prebiotics (nutrient substances that encourage the growth of probiotics in vivo) in their formulations.

Many types of prebiotics are not digested or absorbed in the small intestine but pass into the colon where they stimulate the growth of probiotic bacteria. Fructo-oligosaccharides (FOS) are one type of prebiotic; inulin compounds (which are also oligosaccharides) are another. For these compounds to be effective they must be ingested in relatively large quantities, such as 4-10 grams/day for FOS and 10-14 grams/day for inulin. Probiotics, by comparison, can be effectively administered in milligram quantities, containing $10^7$-$10^{10}$ colony forming units (cfu). Thus, it is impractical to mix FOS or inulin with probiotics and deliver them in capsules or tablets. Further, such carbohydrate type prebiotics often break down to glucose, in vivo, which enhances growth of non-probiotic bacteria, including pathogenic clostridium. Moreover, FOS can cause flatulence and abdominal pain and some people experience severe allergic reactions to inulin. Therefore, there is a need for a non-carbohydrate prebiotic that can be used at low dosage while effectively stimulating probiotic bacteria.

Although enzymes have been used to generate prebiotics under laboratory conditions followed by subsequent feeding of the preformed prebiotics to achieve probiotic stimulation (see U.S. Pat. Nos. 6,791,015 and 6,730,502), no one has suggested using enzymes to generate these effects in vivo. U.S. Pat. No. 5,817,350 discloses the use of the prebiotic enzymes cellulase, amylase and hemicellulase, for use as dietary supplements, but not use of these enzymes to stimulate administered probiotics. Enzymes which can generate compounds which significantly increase probiotic growth or activity without generating significant amounts of glucose or otherwise stimulating growth of undesirable digestive tract bacteria, would be a significant improvement over existing formulations.

Iso-malto oligosaccharides can be enzymatically digested to simpler sugars by inulinase, which is included in some commercially-available probiotic formulations because it digests linear fructans (inulin). Inulin is known to stimulate bifidobacteria growth. Inulin in diet does not lead to a rise in serum glucose or stimulate insulin secretion, but inulinase digestion generates significant fructose. It is not clear whether fructose would preferentially increase growth of probiotics or of competitive digestive tract bacteria, including pathogenic bacteria.

The product Beano™ includes the enzyme alpha-galactosidase, which can break down polysaccharides and oligosaccharides, including iso-malto oligosaccharides, which are in foods such as legumes (beans and peanuts) and cruciferous vegetables (cauliflower, broccoli, cabbage, brussels sprouts, among others). The enzyme breaks those complex sugars into simpler sugars, making these foods somewhat more digestible, and thereby reducing intestinal gas. Beano does not include any probiotics in its formulation.

The hydrolysis of lactose to glucose and galactose is catalyzed by the enzymes lactase and β-galactosidase. Because β-galactosidase would generate glucose from lactose in the diet, it is not preferred for inclusion in probiotics. *Lactobacillus bulgaricus* produces beta-galactosidase, and this strain is a probiotic purported to treat lactose intolerance.

SUMMARY

This disclosure relates to enhancing growth and/or activity of lactobacilli using a prebiotic formulation which includes iso-malto oligosaccharides and α-galactosidase; and to enhancing growth and/or activity of bifidobacteria using a prebiotic formulation which includes iso-malto oligosaccharides and β-glucanase. Other combinations of fibers and enzymes are described below which also stimulate growth and activity of lactobacilli or bifidobacteria.

The enzymes α-galactosidase and β-glucanase react with the fiber prebiotics to generate shorter chain oligosaccharides, some of which are preferential growth enhancers for the probiotics. The enzymes are believed to not generate significant amounts of glucose in the reaction, as it can stimulate growth of undesirable bacterial species.

The fiber prebiotic, the enzyme(s) and the probiotic(s) can be administered in a combined formula, or, the fiber prebiotic with the appropriate enzyme (e.g., α-galactosidase or β-glucanase) can be in media where they can react (e.g., added to foods) and the probiotic can be administered separately. Or, each of these ingredients can be administered separately, whereby the prebiotic and the enzyme can react in vivo, and the probiotic can metabolize the reaction product(s) to enhance its growth and activity.

More specifically, the invention relates to enhancing in vivo growth and/or activity of both lactobacilli and bifidobacteria using iso-malto oligosaccharides as the prebiotic, and both α-galactosidase and β-glucanase as the enzymes. Again, these ingredients can be combined or administered separately.

Pectinase may also be included in any of the formulations described herein. Pectinase are a class of enzymes including pectolyase, pectozyme and polygalacturonase. They break down pectin, a polysaccharide found in the cell walls of plants.

The above formulas could also include other prebiotics (including inulin, wheat dextrin, and partially hydrolyzed guar gum ("PHGG")) and other fiber-digesting enzymes, including Fiberase™ (a combination of cellulase, hemicellulase, pectinase and xylanase). Cellulase includes cellulase-TL and cellulase-AN. The formulas could also include protease enzymes including papain, bromelain, fungal protease, fungal acid-protease, bacterial protease, fungal peptidase, nattokinase, serapeptase, trypsin, chymotrypsin pancreatin and pepsin. Carbohydrase enzymes (including alpha-amylase, amylase, glucoamylase, lactase, and invertase) are generally not preferred in the formula, as they generate glucose.

The above formulas could also include sunflower lecithin and/or oleic acid (as described in U.S. Pat. No. 8,105,577, incorporated by reference) and/or the food grade polysorbate surfactants (as described in U.S. Pat. No. 8,066,986, incorporated by reference): Polysorbate-60, polysorbate-80 or any polysorbate with an HLB>12, where HLB is the hydrophile-lipophile balance, designated from 1 to 20.

The above formulas could also contain other carriers, binders or adsorbents, including but not limited to food grade starches and silicates. The above formulas can be packaged for administration in capsules, tablets or packets, or combinations thereof. Alternatively, they can be added to foods, separately or in combination.

Additional combinations of substrates, enzymes and probiotics which enhanced growth and/or activity of the probiotics are described below and are also within the scope of the inventions herein.

DETAILED DESCRIPTION

Certain enzymes, acting upon certain fiber sources, render the fiber sources a preferential food source (prebiotic) for probiotic bacteria. As shown in the figures, different species of probiotics, all of which are lactic acid producing bacteria, respond differently to various enzymes and fiber sources. All of the enzymes described are "fiber-digesting" enzymes, which render complex oligosaccharides into simpler oligosaccharides, but without significant production of glucose. Particular enzyme/fiber combinations respectively improve both activity and growth of *Lactobacillus* and of Bifidobacteria.

These combinations of enzymes and prebiotics can be used to improve the commercial value and performance of probiotic products, which all include *Lactobacillus* and/or Bifidobacteria. These combinations of enzymes and prebiotics can be formulated with *Lactobacillus* and/or Bifidobacteria, e.g., in a capsule or tablet form. Another use for them would be as food additives to foods that do not requiring heating/boiling before consumption, e.g., yogurt, ice cream, desserts, bread or other bakery goods, snacks, breakfast cereal or candy.

These combinations of enzymes and prebiotics could be added to such foods with or without probiotics, and with or without other growth stimulants for probiotics (e.g., polysorbate 80, sunflower lecithin or oleic acid). If such combinations of enzymes and prebiotics were added, for example, to yogurt, they could act to produce the less complex oligosaccharides after consumption. If the probiotics (with or without other growth stimulants) are ingested near the time the yogurt is consumed, they could metabolize the less complex oligosaccharides present, and thereby have their growth and activity stimulated. Alternatively, the probiotics (with or without other growth stimulants) can be directly added to such foods along with the appropriate combination of enzymes and prebiotics, where they can stimulate probiotic growth after consumption.

Figure 3A:
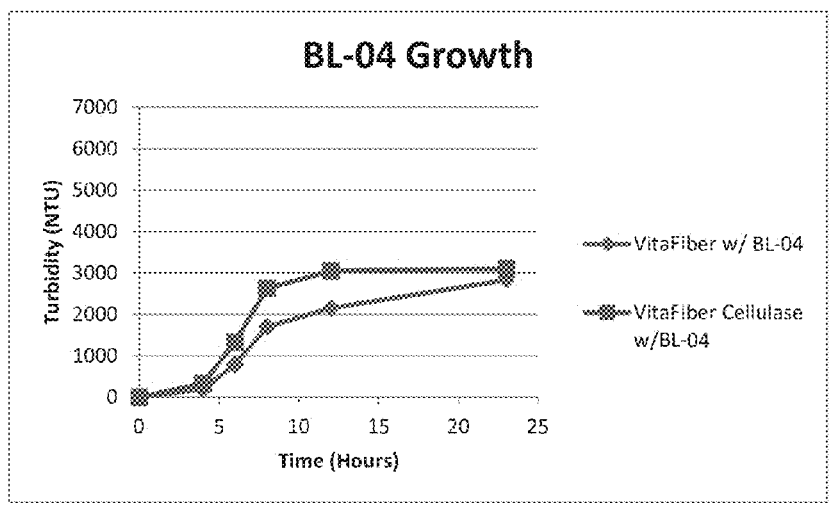
FIG. 3A shows the growth of BL-04 (*Bifidobacterium lactis*) in No-G-Broth with added VitaFiber™ and where VitaFiber™ was pre-digested with cellulase before the remaining No-G-Broth broth ingredients were added.
Figure 4A:
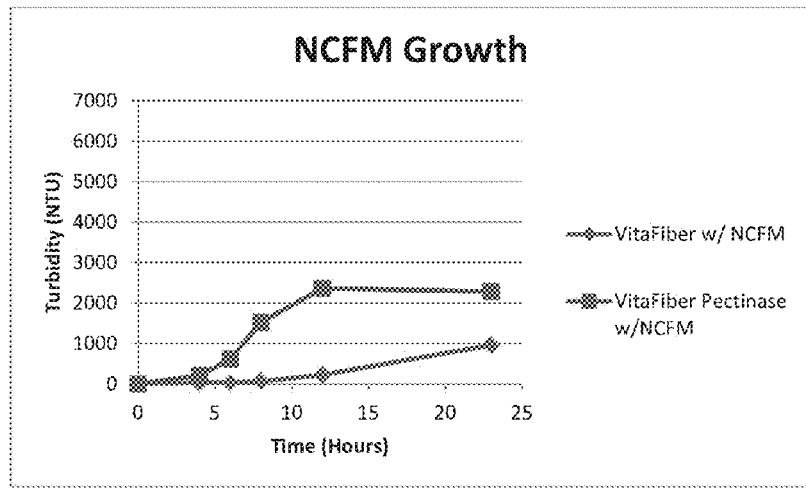
FIG. 4A shows the growth of NCFM (*Lactobacillus acidophilus*) in No-G-Broth with added VitaFiber™, and where VitaFiber™ was pre-digested with pectinase before the remaining No-G-Broth broth ingredients were added.
Figure 5A:
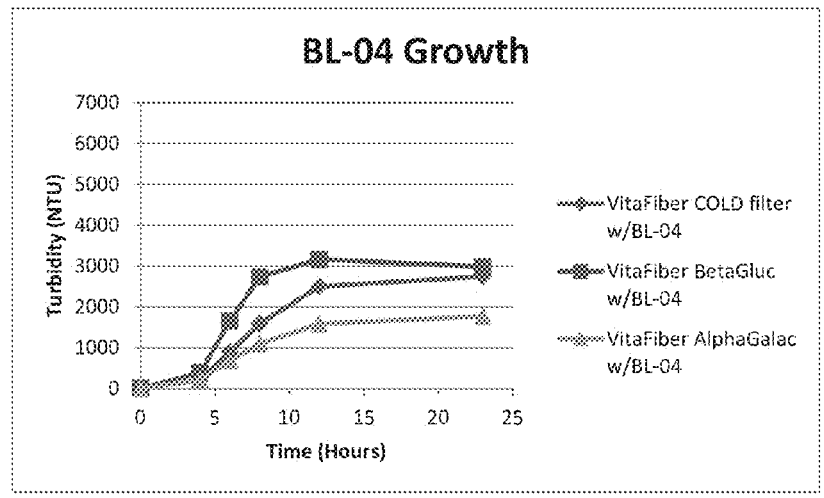
FIG. 5A shows the growth of BL-04 (*Bifidobacterium lactis*) in No-G-Broth with added VitaFiber™, and where VitaFiber™ was pre-digested with either β-glucanase or α-galactosidase before the remaining No-G-Broth broth ingredients were added. The VitaFiber™ was sterilized by filtering it through a sterile 0.22 μm filter, while the MRS broth ingredients in the VitaFiber™ mixture were separately sterilized by autoclaving.
Figure 5B:
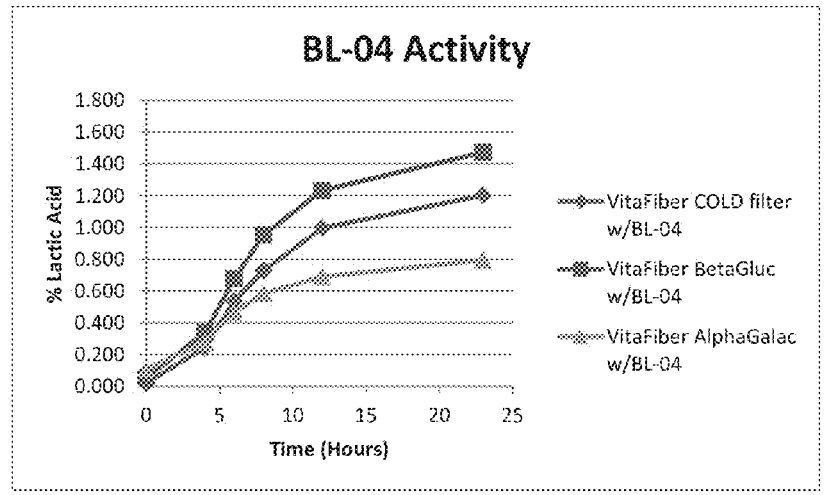
FIG. 5B shows the activity of BL-04 (*Bifidobacterium lactis*) in the same conditions and media as in FIG. 5A.
Figure 6A:
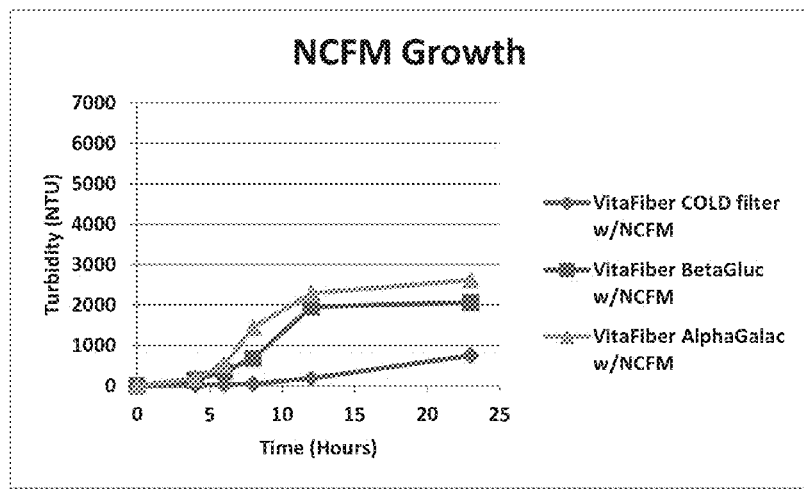
FIG. 6A shows the growth of NCFM (*Lactobacillus acidophilus*) in No-G-Broth with added VitaFiber™, and where VitaFiber™ was pre-digested with either β-glucanase or α-galactosidase before the remaining No-G-Broth broth ingredients were added.
Figure 7A:
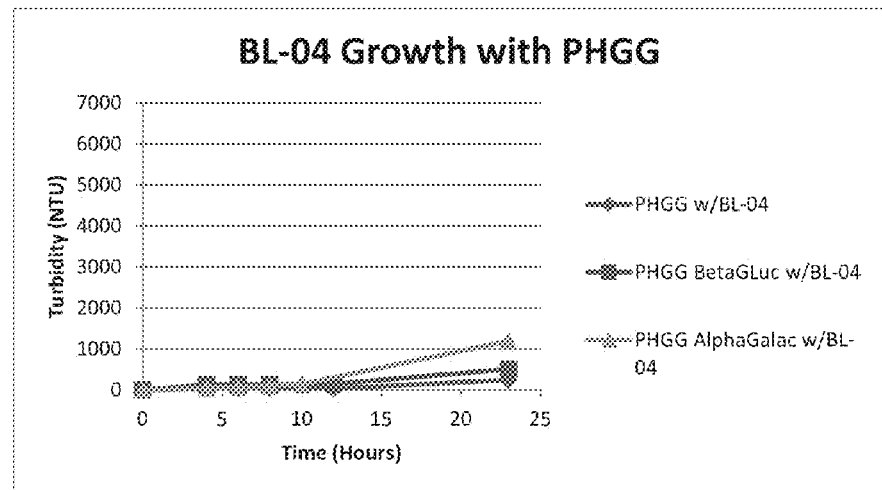
FIG. 7A shows the growth of BL-04 (*Bifidobacterium lactis*) in No-G-Broth where a quantity of partially hydrolyzed guar gum ("PHGG") has been added which is approximately the same as the amount of glucose removed from the starting MRS broth; and where PHGG was pre-digested with either β-glucanase or α-galactosidase before the remaining No-G-Broth broth ingredients were added.
Figure 7B:
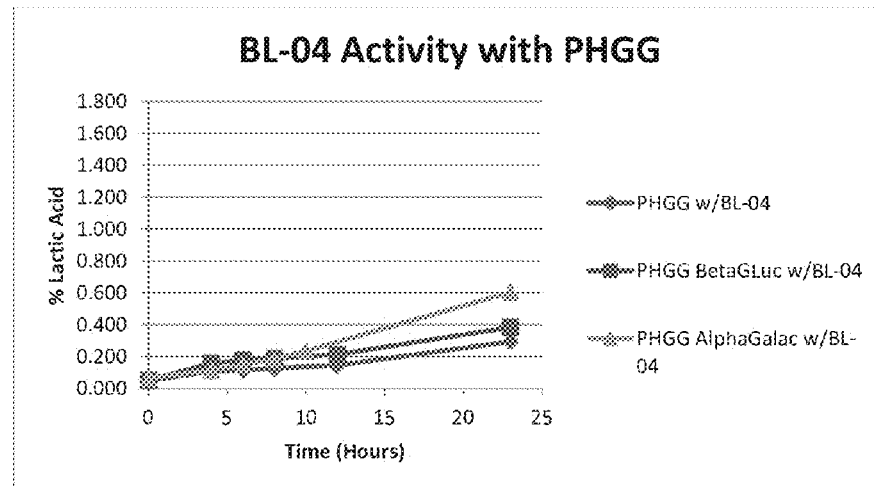
FIG. 7B shows the activity of BL-04 (*Bifidobacterium lactis*) in the same conditions and media as in FIG. 7A.
Figure 8A:
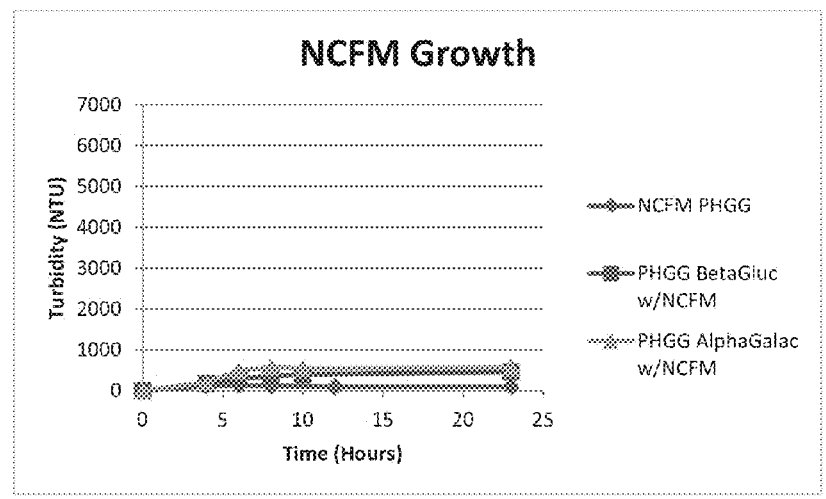
FIG. 8A shows the growth of NCFM (*Lactobacillus acidophilus*) in No-G-Broth where a quantity of partially hydrolyzed guar gum ("PHGG") has been added which is approximately the same as the amount of glucose removed from the starting MRS broth; and where PHGG was pre-digested with either β-glucanase or α-galactosidase before the remaining No-G-Broth broth ingredients were added.
Figure 8B:
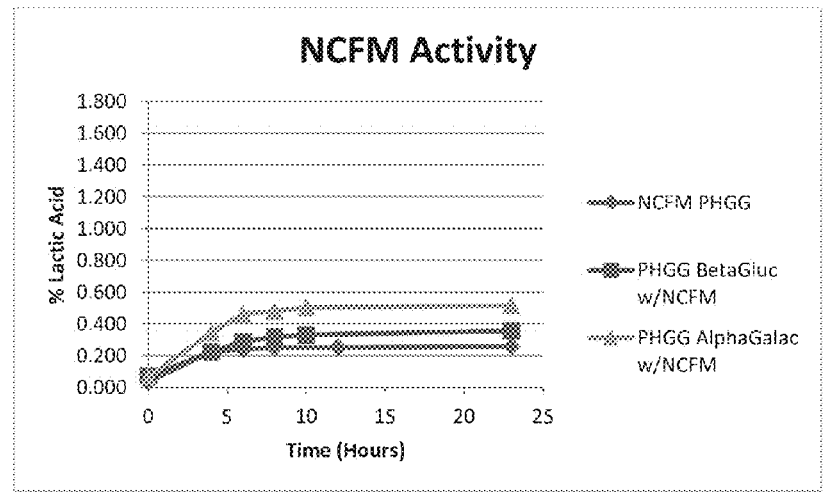
FIG. 8B shows the activity of NCFM (*Lactobacillus acidophilus*) in the same conditions and media as in FIG. 8A.
Figure 9A:
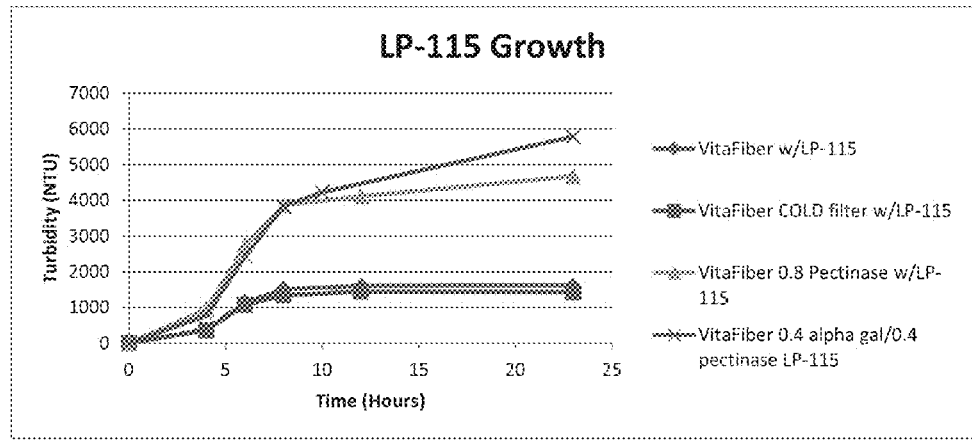
FIG. 9A shows the growth of LP-115 (*Lactobacillus plantarum*) in No-G-Broth with added VitaFiber™, and where VitaFiber™ was pre-digested with either with either pectinase or a 50:50 mixture of α-galatosidase plus pectinase before the remaining No-G-Broth ingredients were added. Note that "cold filter" means the VitaFiber™ was sterilized by filtering it through a sterile 0.22 μm filter, while the MRS broth ingredients in the VitaFiber™ mixture were separately sterilized by autoclaving.
Figure 9B:
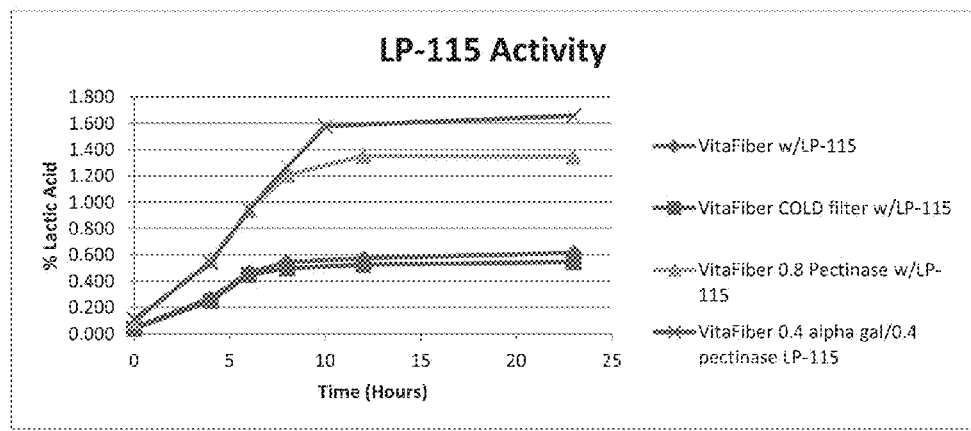
FIG. 9B shows the activity of LP-115 (*Lactobacillus plantarum*) in the same conditions and media as in FIG. 9A.
Figure 13A:
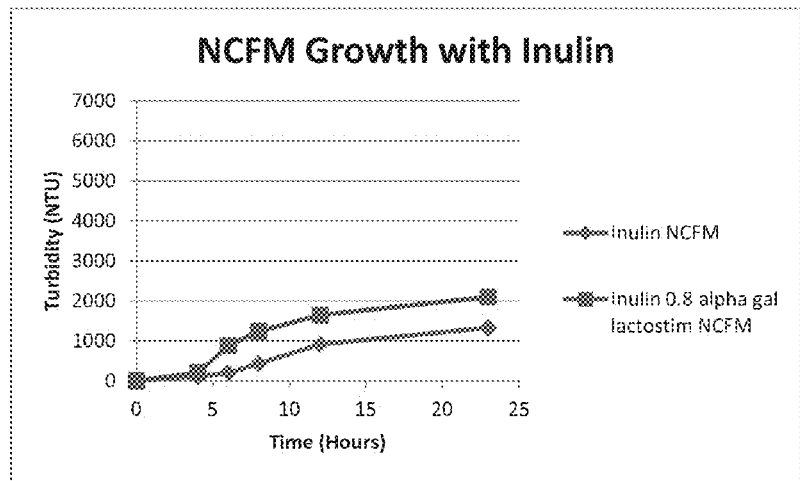
FIG. 13A shows the growth of NCFM (*Lactobacillus acidophilus*) in No-G-Broth with inulin substituted for glucose, and where inulin was pre-digested with α-galactosidase before the remaining No-G-Broth ingredients (except polysorbate 80) were added along with added LactoStim™.
Figure 13B:
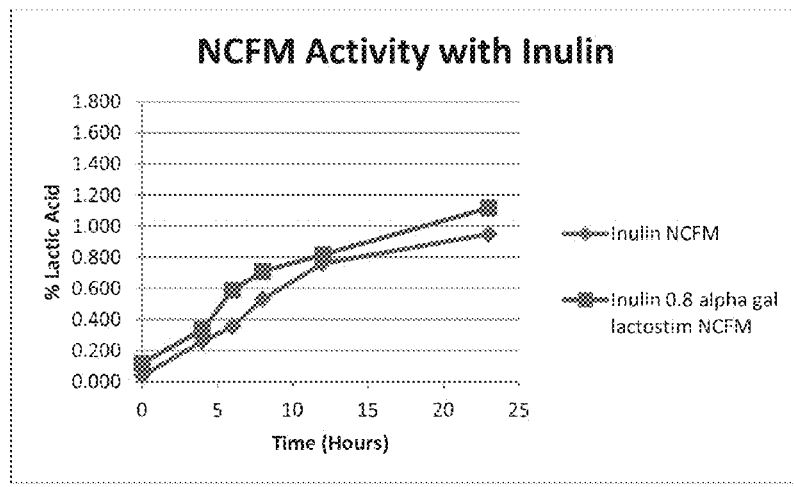
FIG. 13B shows the activity of NCFM (*Lactobacillus acidophilus*) in the same conditions and media as in FIG. 13A.
Figure 25A:
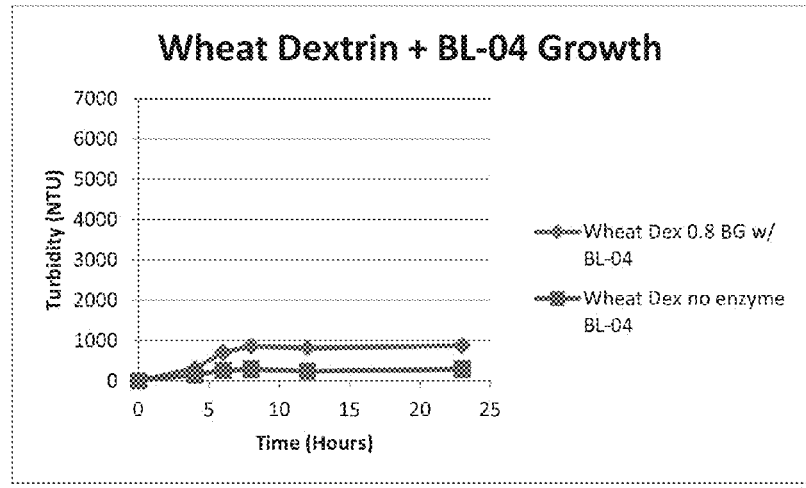
FIG. 25A shows the growth of *Bifidobacterium lactis* (BL-04) with Wheat Dextrin in No-G-Broth, and where Wheat Dextrin was pre-digested with β-glucanase before adding the other ingredients in No-G-Broth.
Figure 28A:
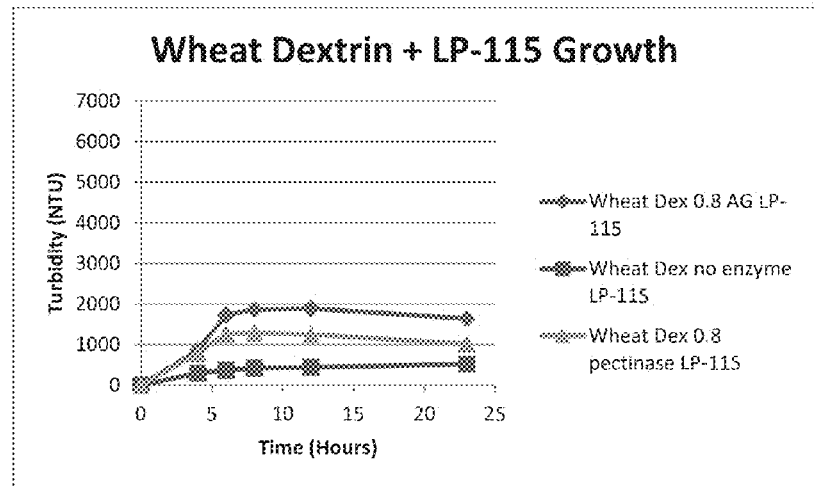
FIG. 28A shows the growth of *Lactobacillus plantarum* (LP-115) with Wheat Dextrin in No-G-Broth, and where Wheat Dextrin was pre-digested with either pectinase or α-galactosidase before adding the other ingredients in No-G-Broth.
Figure 28B:
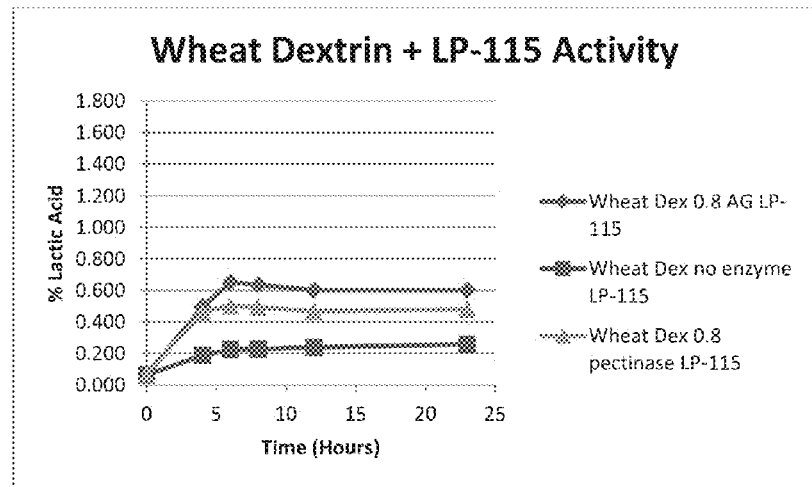
FIG. 28B shows the activity of *Lactobacillus plantarum* (LP-115) in the same conditions and media as in FIG. 28A.

The combinations of enzymes and fiber sources which were shown to significantly enhance growth and activity of particular probiotics without glucose in the growth media are (note that VitaFiber™ is substantially isomalto-oligosaccharide, as shown in Table 1):

α-galactosidase with isomalto-oligosaccharide enhanced growth and activity of *lactobacillus* (see FIGS. 6A; 6B; FIGS. 9A; 9B; 10A; 10B; 15A; 15B; 16A; 16B; 17A, 17B-20A, 20B);

β-glucanase with isomalto-oligosaccharide enhanced growth and activity of *bifidobacterium* (see FIGS. 5A, 5B; 11A; 11B; 16A; 16B; 14A; 14B and 21A, 21B);

α-galactosidase with partially hydrolyzed guar gum enhanced growth and activity of *bifidobacterium* (see FIGS. 7A; 7B);

β-glucanase with partially hydrolyzed guar gum enhanced growth and activity of *lactobacillus* (see FIGS. 8A, 8B);

α-galactosidase with partially hydrolyzed guar gum enhanced growth and activity of *lactobacillus* (see FIGS. 8A, 8B);

α-galactosidase with inulin enhanced growth and activity of *lactobacillus* (see FIGS. 13A, 13B);

α-galactosidase with wheat dextrin enhanced growth and activity of *lactobacillus* (see FIGS. 22A, 22B-24A, 24B; 28A, 28B);

pectinase with wheat dextrin enhanced growth and activity of *lactobacillus* (see FIGS. 28A, 28B);

pectinase with isomalto-oligosaccharide enhanced growth and activity of *lactobacillus* (see FIGS. 4A; 4B; 9A; 9B; 10A; 10B);

β-glucanase with wheat dextrin enhanced growth and activity of *bifidobacterium* (see FIGS. 25A; 25B-27A; 27B);

cellulase with isomalto-oligosaccharide enhanced growth and activity of *bifidobacterium* (see FIGS. 3A; 3B)

Tables 1, 2 and 3 below specify the fiber sources, probiotic species/strains, and the enzymes used in the Examples, which generated the results shown in the figures.

TABLE 1

| Fiber | Brand | Source |
|---|---|---|
| Partially Hydrolyzed Guar Gum (PHGG) | Sunfiber ® | Taiyo International |
| Isomalto-oligosaccharide | VitaFiber ™ | BioNeutra |
| Inulin | Oliggo-Fiber ™ Instant | Cargill |
| Wheat Dextrin | Benefiber ® | Novartis |

TABLE 2

| Probiotic | Strain Designation | Source |
|---|---|---|
| *Bifidobacterium lactis* | BL-04 (BL-34) | Danisco/DuPont |
| *Bifidobacterium lactis* | Bi-07 | Danisco/DuPont |
| *Lactobacillus acidophilus* | NCFM (LA-1) | Danisco/DuPont |
| *Lactobacillus paracasei* | LPC-37 (F-19) | Danisco/DuPont |
| *Lactobacillus rhamnosus* | Lr-32 (LR-44) | Danisco/DuPont |
| *Lactobacillus plantarum* | LP-115 (LP-29) | Danisco/DuPont |
| *Lactobacillus salivarius* | LS-33 (LS-30) | Danisco/DuPont |
| *Bifidobacterium breve* | BB-03 | Danisco/DuPont |

TABLE 3

| Enzyme | Units | Source |
|---|---|---|
| Cellulase | 150,000 CU/gm | BioCat |
| Hemicellulase | 400,000 HCU/gm | BioCat |
| Pectinase | 3,500 endo-PG/gm | BioCat |
| Xylanase | 150,000 XU/gm | BioCat |
| β-Glucanase | 3,000 BGU/gm | BioCat |
| α-Galactosidase | 15,000 GALU/gm | BioCat |
| Fiberase (CHPX) | | BioCat |
| Cellulase | 48,000 CU/gm | |
| Hemicellulase | 102,400 HCU/gm | |
| Pectinase | 420 endo-PG/gm | |
| Xylanase | 25,000 XU/gm | |

Tables 3A and 3B below explain the units used in Table 3 above.

TABLE 3A

| Enzyme Unit Abbreviation | Enzymatic Unit | Reference Method |
|---|---|---|
| CU | Cellulase unit | FCC $8^{th}$ Edition |
| HCU | Hemicellulase unit | FCC $8^{th}$ Edition |
| endo-PG | endo-Polygalacturonase unit | Genencor International Procedure No. ME 400.39, 1981 |
| XU | Xylanase unit | 1989. Appl. Microbiol. Biotechnol. 30: 5-10 |
| BGU | β-Glucanase unit | Novozymes, EB-0338.02/01 |
| GALU | α-Galactosidase unit | FCC $8^{th}$ Edition |

TABLE 3B

| Enzymatic Unit | Definition |
|---|---|
| Cellulase unit | The amount of activity that will produce a relative fluidity change of 1 in 5 minutes in a defined carboxymethyl cellulose substrate under the conditions of the assay at 40° C. |
| Hemicellulase unit | That activity that will produce a relative fluidity change of 1 over a period of 5 minutes in a locust bean gum substrate. |
| Endo-Polygalacturonase unit | The amount of enzyme that reduces the viscosity of the pectin solution by 50% per minute under the conditions of the assay. |
| Xylanase unit | The quantity of enzyme that will liberate 1 μmol per minute of xylose from wheat arabinoxylan under defined conditions of temperature and pH. |
| β-Glucanase unit | The amount of enzyme which liberates glucose to 1 μmol glucose per minute. |
| α-Galactosidase unit | The quantity of enzyme that will liberate 1 μmol per minute of p-nitrophenol under the conditions of the assay. |

Preparing the Growth Media

For the growth and activity determinations described below and shown in the figures, the starting media composition was MRS broth, which was modified as described below.

MRS broth (including the MRS broth labeled "control-scratch" in FIGS. 1A, 1B, 2A, 2B) consisted of the following:

| | |
|---|---|
| Proteose Peptone #3 | 4.0 gms |
| Beef Extract | 4.0 gms |
| Yeast Extract | 2.0 gms |
| Glucose (or substitute ingredient) | 8.0 gms |
| Polysorbate 80 (or LactoStim ®) | 0.4 gms |
| Ammonium Citrate | 0.8 gms |
| Sodium Acetate | 2.0 gms |
| Magnesium Sulfate | 0.04 gms |
| Manganese Sulfate | 0.02 gms |
| Dipotassium Phosphate | 0.8 gms |
| DI Water | 400 mls |

As noted, the starting MRS broth (by Difco™), included glucose. The glucose was removed to generate No-G-Broth, and then an equivalent quantity of one of the fiber sources in Table 1 (i.e., VitaFiber™, PHGG, Inulin or Wheat Dextrin) was added into the No-G-Broth broth, to generate each In different formulations noted in the figures and their description. In cases where an enzyme is included in the formulation in the figures and their description, the enzyme and the fiber were first reacted, then the remaining ingredients in the No-G-Broth were added (as described further below). In cases where LacoStim™ is included, following the reaction between the enzyme and fiber, the remaining ingredients in No-G-Broth were added, but not polysorbate 80.

To determine growth and activity with different media, enzymes and bacterial strains, the fiber source was substituted for glucose in MRS broth and filled into 500 ml flasks, which were then autoclaved at 121° C. for 15 minutes. Each flask was tempered to 37° C. and aseptically inoculated with 0.14 gram (Table 4) of one of the freeze-dried probiotic strain(s) listed in Table 2. The CFUs (colony forming units) of 0.14 gram of each strain in Table 2 is shown in the right-hand column in Table 4.

TABLE 4

| Probiotic species | Strain | CFUs from 0.14 gram |
|---|---|---|
| Bifidobacterium lactis | BL-04 (BL-34) | $134.4 \times 10^9$ |
| Bifidobacterium lactis | Bi-07 | $92.4 \times 10^9$ |
| Lactobacillus acidophilus | NCFM (LA-1) | $54.6 \times 10^9$ |
| Lactobacillus paracasei | LPC-37 (F-19) | $42 \times 10^9$ |
| Lactobacillus rhamnosus | Lr-32 (LR-44) | $31.5 \times 10^9$ |
| Lactobacillus plantarum | LP-115 (LP-29) | $88.9 \times 10^9$ |
| Lactobacillus salivarius | LS-33 (LS-30) | $88.2 \times 10^9$ |
| Bifidobacterium breve | BB-03 | $42 \times 10^9$ |

At specific time intervals, a 30 ml sample from each flask was aseptically transferred into a HACH 2100N Turbidimeter cell. The turbidity of each sample was read and the turbidity results were reported in NTU's, where greater turbidity indicates greater growth. The same 30 ml sample that was used for the turbidity reading was transferred into a 250 ml glass beaker, and the pH was recorded. The sample was then titrated using 0.1N NaOH to an end point of pH 6.8, and the quantity of NaOH used was recorded. The % Lactic Acid was calculated using the following formula:

$$\% \text{ Lactic Acid} = \frac{\text{Lactic Acid} = ((\text{mls of } 0.1\text{N NaOH}) \times (90 \text{ gm/mole}) \times (1 \text{ L}/1000 \text{ ml})) \times 100}{\text{mls of sample}}$$

$$\% \text{ Lactic Acid} = \frac{(\text{mls of } 0.1\text{N NaOH}) \times (0.9)}{30}$$

Higher % Lactic acid indicates higher activity. For samples that were pre-digested with enzymes, the fiber source (table 1) was added to 400 mls of de-ionized water along with the enzyme(s) and incubated for 24 hours in a 37° C. water bath. The remaining MRS components (as specified in the figures and their description) were then added to each flask and autoclaved at 121° C. for 15 minutes. Each flask was tempered to 37° C. and aseptically inoculated with 0.14 gram of the specified probiotic strain(s). At specific time intervals, 30 ml samples were aseptically taken and the turbidity, pH and % Lactic Acid was determined for each flask as described above. All probiotics were held at −10° F. prior to use. All enzymes were held at 5° C. prior to use.

EXAMPLE#1

Figure 1A:
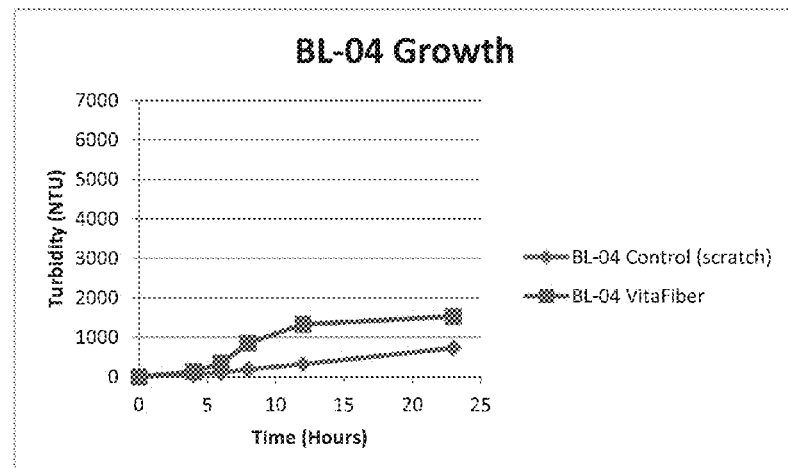
FIG. 1A shows the growth of BL-04 (*Bifidobacterium lactis*) in MRS broth ("Control (scratch)") made by the experimenter to have the same constituents as commercial MRS broth (by Difco™), and its growth in modified MRS broth where the glucose has been removed and a quantity of fiber (in this case, VitaFiber™, by BioNeutra) has been added which is approximately the same as the amount of glucose removed (hereinafter, such modified MRS broth is referred to as "No-G-Broth").
Figure 1B:
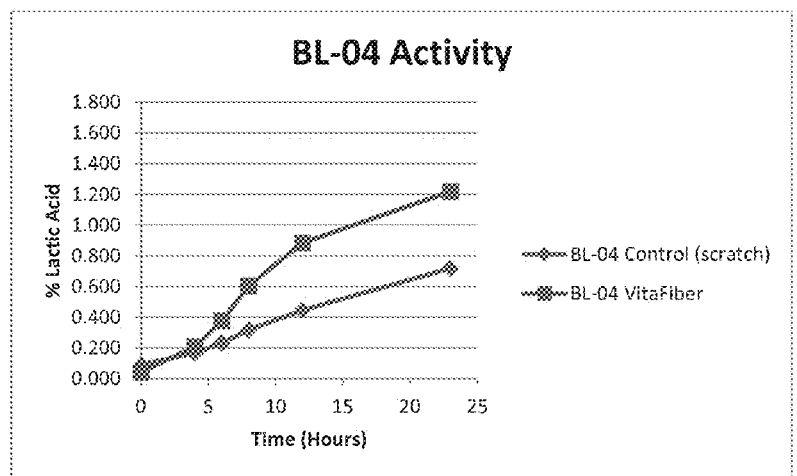
FIG. 1B shows the activity of BL-04 (*Bifidobacterium lactis*) in MRS broth, and in No-G-Broth with added VitaFiber™
Figure 2A:
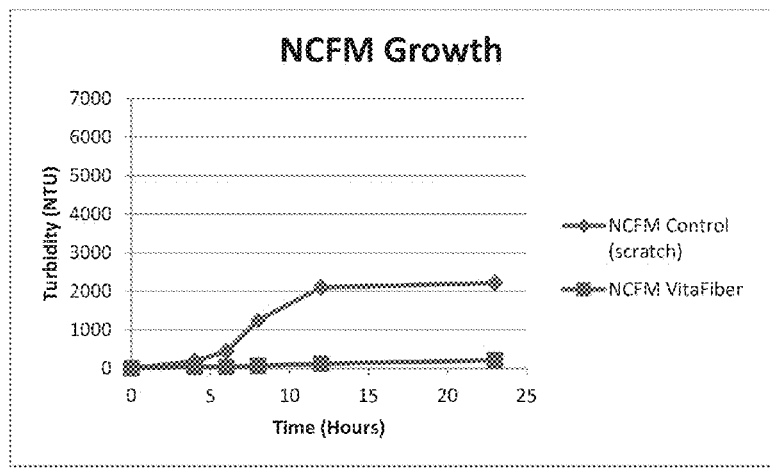
FIG. 2A shows the growth of NCFM (*Lactobacillus acidophilus*) in MRS broth, and in No-G-Broth with added VitaFiber™ as in FIGS. 1A, 1B.
Figure 2B:
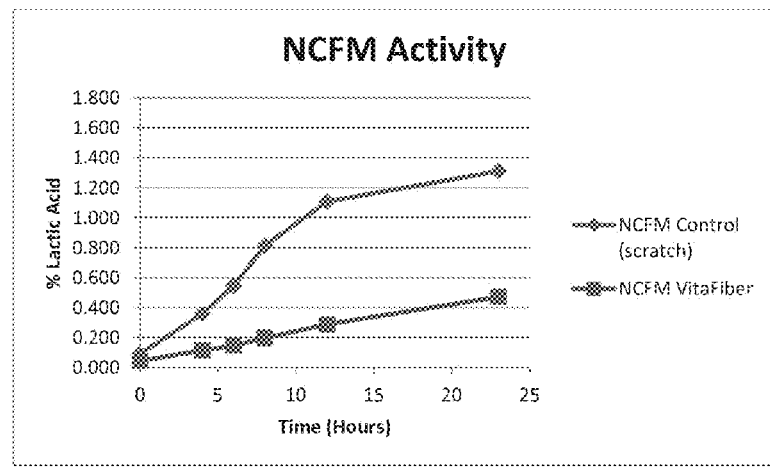
FIG. 2B shows the activity of NCFM (*Lactobacillus acidophilus*) in MRS broth, and in No-G-Broth with added VitaFiber™ as in FIGS. 1A, 1B.

Isomalto-oligosaccharide prebiotic (VitaFiber™) was substituted as the carbohydrate source in MRS broth, replacing glucose. Growth of *Bifidobacterium lactis* (BL-04) and *Lactobacillus acidophilus* (NCFM) were monitored. BL-04 grew better with the isomalto-oligosaccharide than with glucose (FIG. 1A). NCFM growth was stimulated by the isomalto-oligosaccharide, however, not as much as with the glucose control (FIG. 2A).

EXAMPLE#2

Figure 3B:
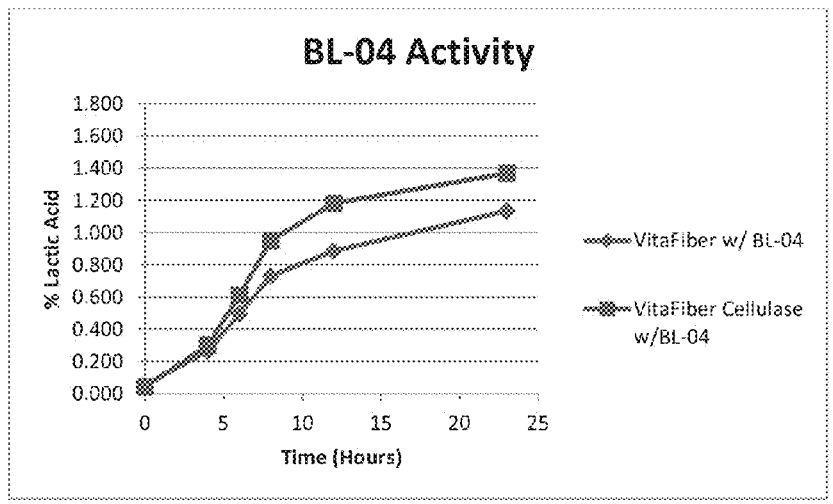
FIG. 3B shows the activity of BL-04 (*Bifidobacterium lactis*) in No-G-Broth with added VitaFiber™, and where VitaFiber™ was pre-digested with cellulase before the remaining No-G-Broth broth ingredients were added.
Figure 4B:
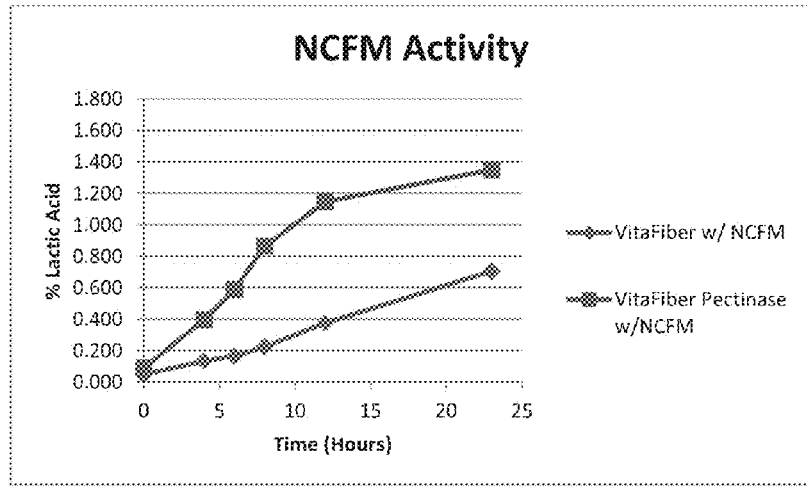
FIG. 4B shows the activity of NCFM (*Lactobacillus acidophilus*) in No-G-Broth with added VitaFiber™, and where VitaFiber™ was pre-digested with pectinase before the remaining No-G-Broth broth ingredients were added.

Isomalto-oligosaccharide (VitaFiber™) was digested for 24 hours in a 37° C. water bath with 0.2% (w/v) of various enzymes. Enzymes tested were either Fiberase™ (which is a combination of cellulase, hemicellulase, pectinase and xylanase), and cellulase, hemicellulase, pectinase and xylanase were also tested individually. Digesting VitaFiber™ (VF) with Fiberase™, cellulase, hemicellulase or xylanase gave a higher activity for BL-04 than undigested VF. Pectinase did not. The highest activity occurred with cellulase (1.368% lactic acid) (FIG. 3B). All flasks with enzyme digested fiber and NCFM had a higher activity than the undigested fiber control. In the case of NCFM, pectinase (FIG. 4B) gave the highest activity with 1.350% lactic acid produced.

EXAMPLE#3

Figure 6B:
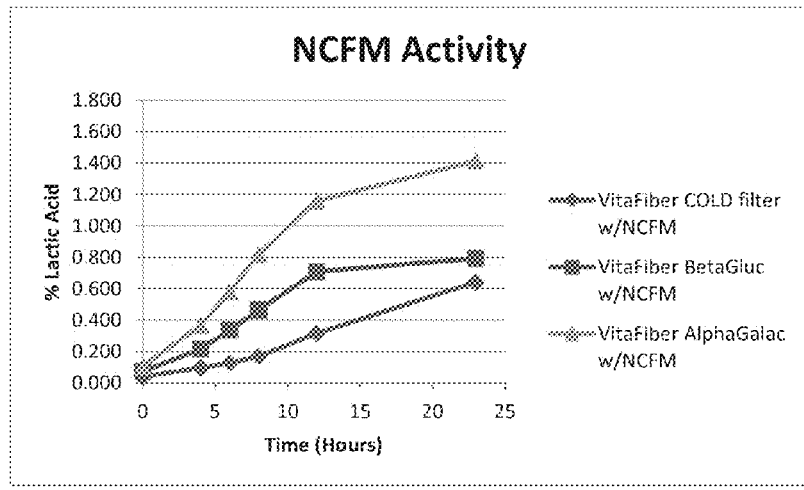
FIG. 6B shows the activity of NCFM (*Lactobacillus acidophilus*) in the same conditions and media as in FIG. 6A.

VitaFiber™ (VF) was digested with either 0.2% (wt/vol) β-glucanase or 0.2% (wt/vol) α-galactosidase and inoculated with either BL-04 or NCFM. Undigested, unheated controls were also tested, replacing media autoclaved with VF with cold filtered VF. For NCFM, VF digested with α-galactosidase had the highest activity, producing 1.413% lactic acid (FIG. 5B). For BL-04, VF digested with β-glucanase had the highest activity, producing 1.473% lactic acid (FIG. 6B). The enzyme used to digest VitaFiber™ (VF) appears to stimulate specific bacteria. VF digested with β-glucanase stimulates BL-04, but it does not have the same effect on NCFM. VF digested with α-galactosidase stimulates NCFM, but does not have the same effect on BL-04.

EXAMPLE#4

Another prebiotic fiber source, PHGG (partially hydrolyzed guar gum), was digested with 0.2% (wt/vol) β-glucanase or 0.2% (wt/vol) α-galactosidase but showed little stimulation of either Bidfidobacterium *lactis* (FIGS. 7A; 7B) or *Lactobacillus acidophilus* (FIG. 8A; 8B).

EXAMPLE#5

*Lactobacillus plantarum* (LP-115), was assayed in both undigested VF, VF digested with 0.2% (wt/vol) pectinase or a blend of 0.1% (wt/vol) pectinase plus 0.1% (wt/vol) α-galactosidase (FIGS. 9A; 9B). The activity of VF digested with 0.1% pectinase plus 0.1% α-galatosidase had an activity of 1.656% lactic acid. The blended enzyme digestion had a higher activity than pectinase alone.

EXAMPLE#6

Figure 10A:
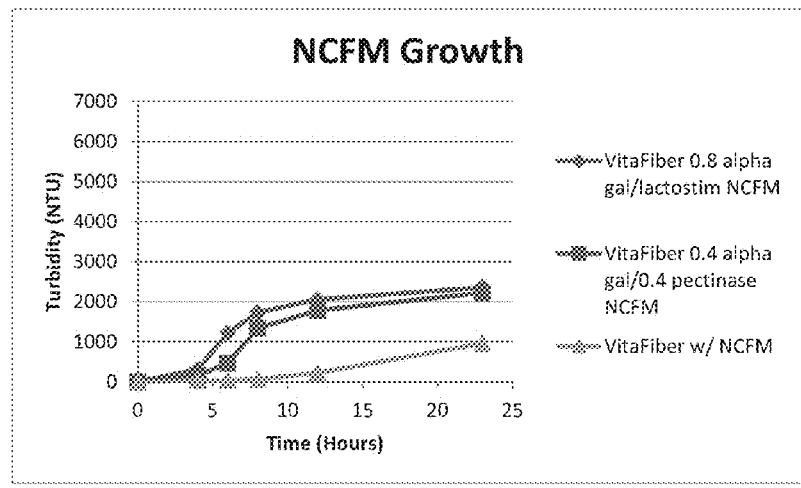
FIG. 10A shows the growth of NCFM (*Lactobacillus acidophilus*) where VitaFiber™ was pre-digested with α-galactosidase before the remaining No-G-Broth ingredients (except polysorbate 80) were added along with added LactoStim™ (sunflower lecithin and oleic acid). VitaFiber™ was also pre-digested with α-galactosidase plus pectinase, before the remaining No-G-Broth ingredients were added.
Figure 10B:
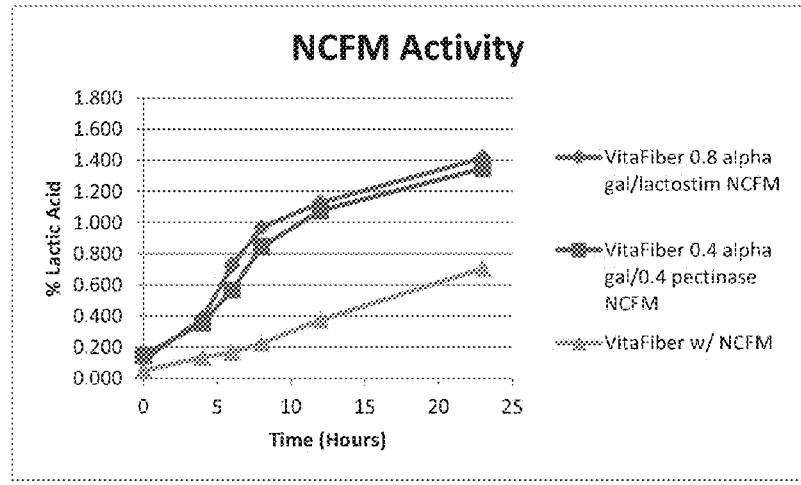
FIG. 10B shows the activity of NCFM (*Lactobacillus acidophilus*) in the same conditions and media as in FIG. 10A.
Figure 11A:
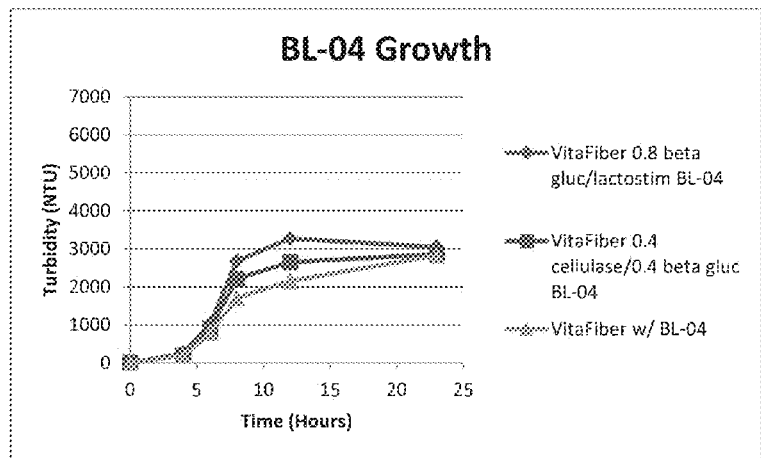
FIG. 11A shows the growth of BL-04 (*Bifidobacterium lactis*) where VitaFiber™ was pre-digested with β-glucanase before the remaining No-G-Broth ingredients (except polysorbate 80) were added along with added LactoStim™, and where VitaFiber™ was pre-digested with β-glucanase and cellulase before the remaining No-G-Broth ingredients were added.
Figure 11B:
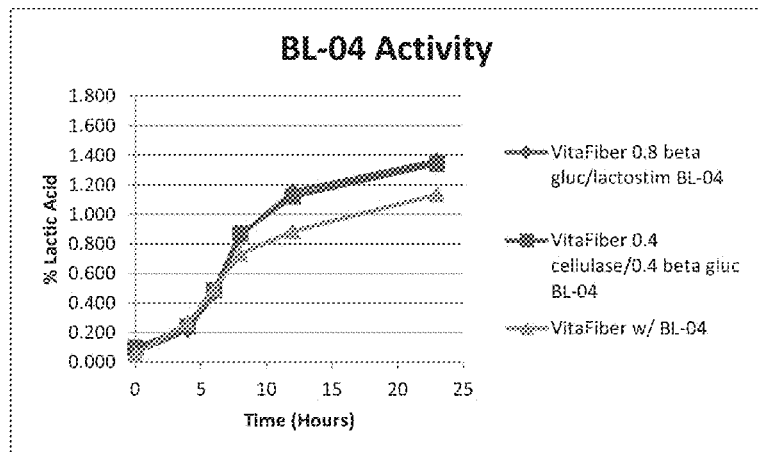
FIG. 11B shows the growth of BL-04 (*Bifidobacterium lactis*) in the same conditions and media as in FIG. 11A.

VitaFiber™ (VF) was digested with equal amounts (by weight) of two enzymes for each strain. *Bifidobacterium lactis* (BL-04) was inoculated into VF digested with 50:50 (wt:wt), cellulase/β-glucanase (0.2% w/vol). *Lactobacillus acidophilus* (NCFM) was inoculated into VF digested with 50:50 (wt:wt), pectinase/α-galatosidase (0.2% w/vol). LactoStim™ (0.1%) was added with the other ingredients for MRS broth (but not glucose or polysorbate 80) following digestion. Ex. 3 (FIGS. 5A; 5B; 6A; 6B) demonstrates that β-glucanase is the preferred enzyme for growing BL-04 and that α-galactosidase is the preferred enzyme for growing NCFM. VF digested with α-galactosidase, followed by adding LactoStim™, had an activity of 1.416% lactic acid for NCFM (FIG. 10B). The addition of LactoStim™ thus generated a slight increase in activity, when these results are compared to the FIG. 5B results. VF digested with β-glucanase followed by adding LactoStim™, had an activity of 1.365% lactic acid (FIG. 11B) for BL-04. The addition of LactoStim™ thus generated a slight decrease in activity, as seen when these results are compared to the FIG. 6B results. LactoStim™ is a patented probiotic stimulant protected by U.S. Pat. Nos. 8,105,576 and 8,105,577.

EXAMPLE#7

Figure 12A:
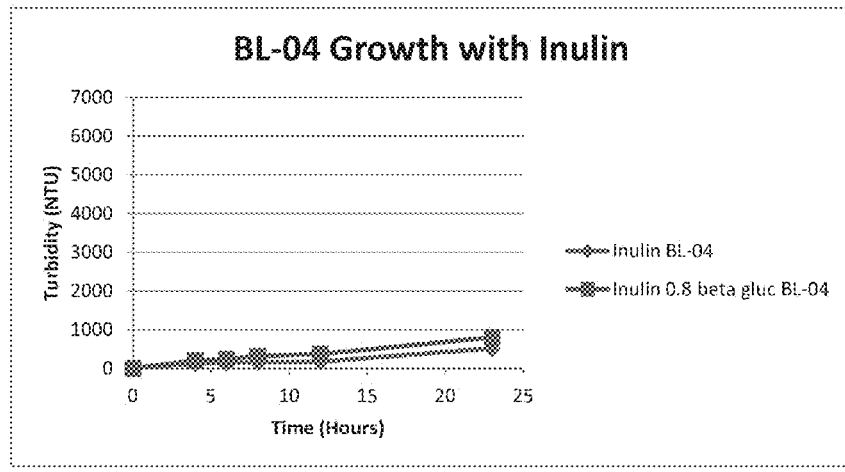
FIG. 12A shows the growth of BL-04 (*Bifidobacterium lactis*) in No-G-Broth where a quantity of inulin has been added which is approximately the same as the amount of glucose removed from the starting MRS broth, and where inulin was pre-digested with β-glucanase before the remaining No-G-Broth ingredients were added.
Figure 12B:
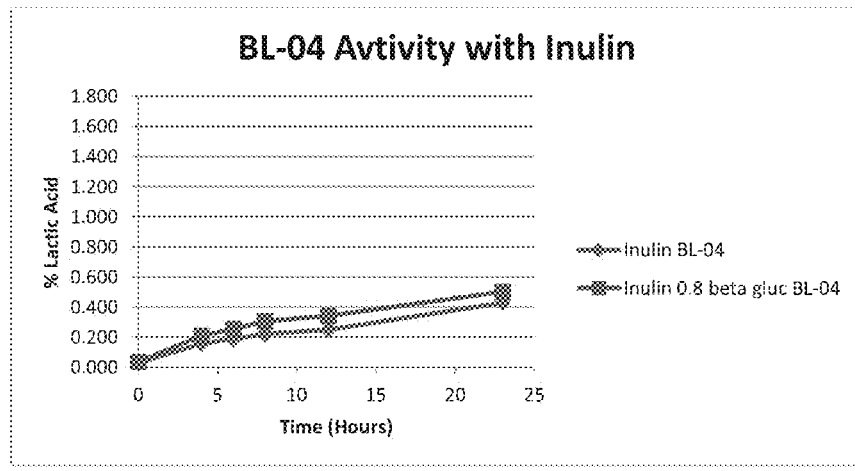
FIG. 12B shows the activity of BL-04 (*Bifidobacterium lactis*) in the same conditions and media as in FIG. 12A.

Inulin was used as the fiber source in testing the growth and activity of *Bifidobacterium lactis* (BL-04). Inulin was digested with 0.2% (wt/vol) β-glucanase (FIGS. 12A; 12B). *Lactobacillus acidophilus* (NCFM) was tested with inulin or inulin digested with 0.2% (wt/vol) α-galatosidase, both with and without addition of 0.1% (wt/vol) LactoStim™ following digestion (FIGS. 13A; 13B). Digested inulin showed a small increase in activity.

EXAMPLE#8

Figure 14A:
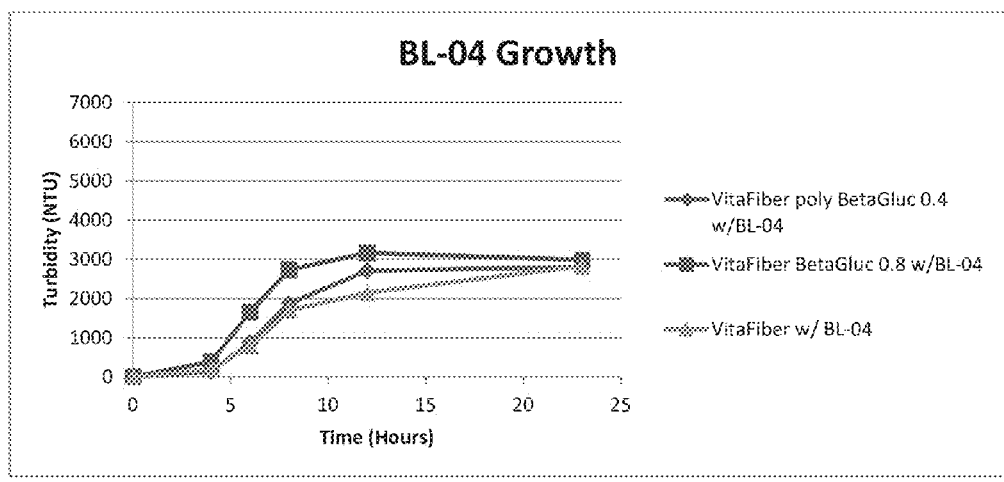
FIG. 14A shows the growth of BL-04 (*Bifidobacterium lactis*) in No-G-Broth with VitaFiber™ substituted for glucose, and where VitaFiber™ was pre-digested with one of two different concentrations of β-glucanase before the remaining No-G-Broth ingredients were added.
Figure 14B:
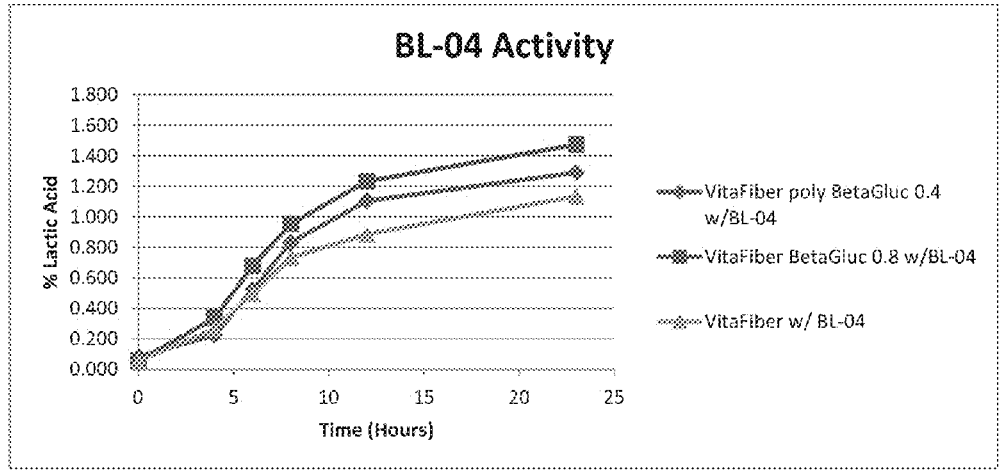
FIG. 14B shows the activity of BL-04 (*Bifidobacterium lactis*) in the same conditions and media as in FIG. 14A.
Figure 15A:
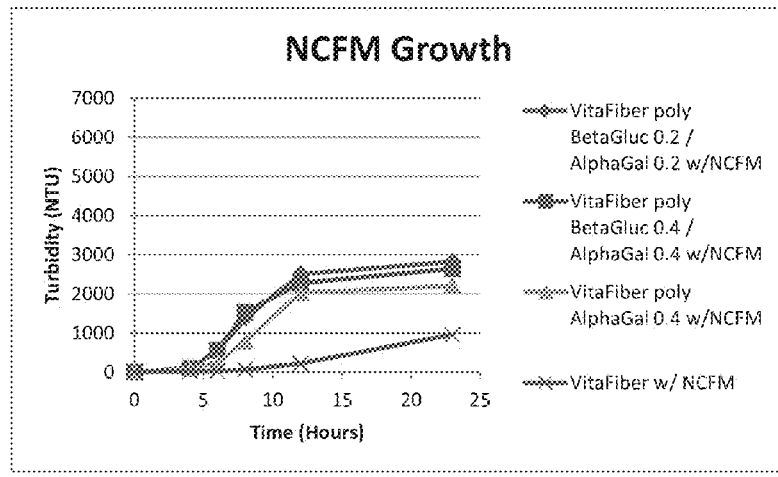
FIG. 15A shows the growth of NCFM (*Lactobacillus acidophilus*) in No-G-Broth with VitaFiber™ substituted for glucose, and where VitaFiber™ was pre-digested with one of: (i) α-galactosidase; (ii) a lower concentration of α-galactosidase and β-glucanase; and (iii) a higher concentration of α-galactosidase and β-glucanase.
Figure 15B:
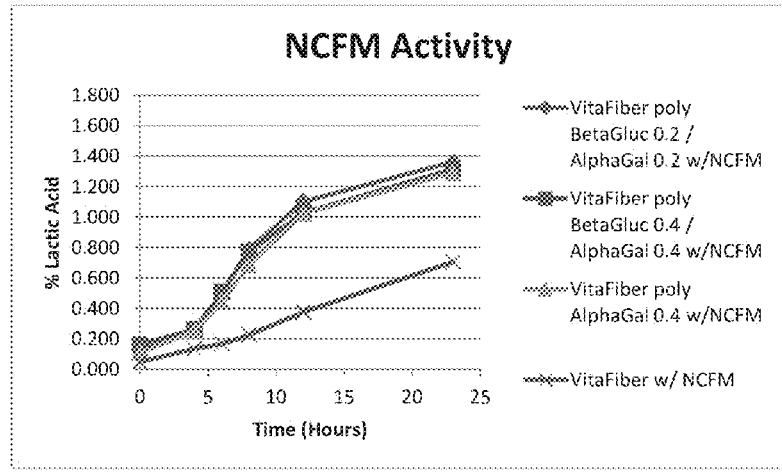
FIG. 15B shows the activity of NCFM (*Lactobacillus acidophilus*) in the conditions and same media as in FIG. 15A.

VitaFiber™ was digested with varied amounts of either a combination of 50:50 (wt:wt) β-glucanase plus α-galactosidase, β-glucanase alone, or α-galatosidase alone. VF digested with half the amount of β-glucanase (0.1% w/vol) had an activity of 1.290% lactic acid for BL-04. This activity was less than when 0.2% (w/vol) β-glucanase was used to digest VF (FIG. 14B). Digesting VF with 0.05% (wt/vol) β-glucanase plus 0.05% (wt/vol) α-galactosidase had an activity of 1.362% lactic acid for NCFM, while digesting VF with 0.1% (wt/vol) β-glucanase plus 0.1% (wt/vol) α-galactosidase had an activity of 1.314% lactic acid for NCFM. Digesting VF with 0.1% (w/vol) α-galactosidase alone had an activity of 1.290% lactic acid for NCFM (FIG. 15B).

EXAMPLE#9

Figure 16A:
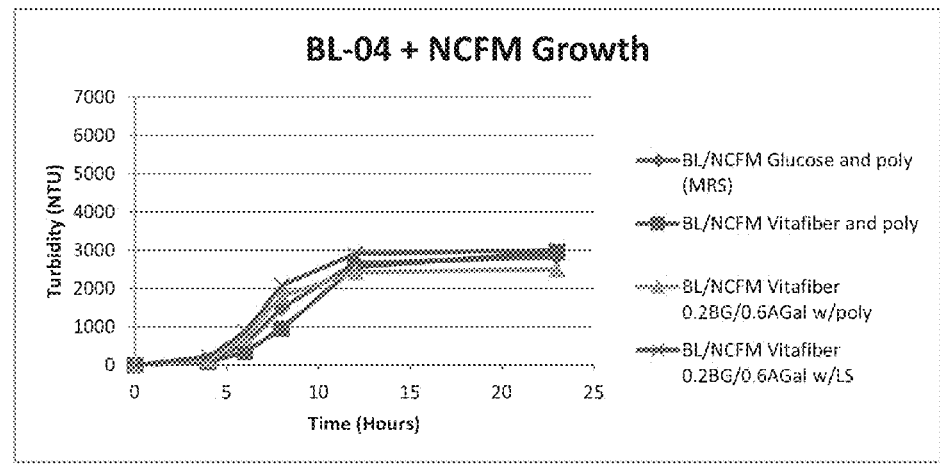
FIG. 16A shows the growth of BL-04 and NCFM (i) in MRS broth, (ii) in No-G-Broth with VitaFiber™ substituted for glucose, (ii) where VitaFiber™ was pre-digested with a 1:3 blend of 3-glucanase and α-galactosidase before (a) adding the other ingredients in No-G-Broth, (b) adding LactoStim™ and the other ingredients in No-G-Broth but not polysorbate 80.
Figure 16B:
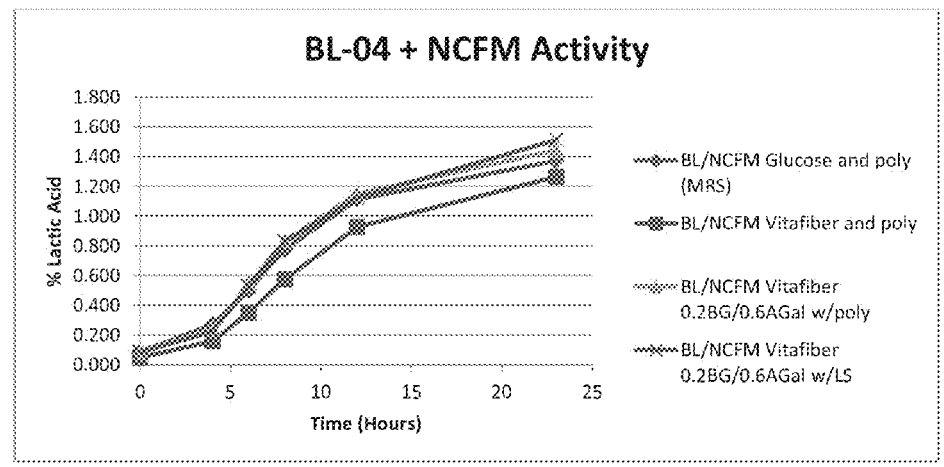
FIG. 16B shows the activity of BL-04 and NCFM in the same conditions and media as in FIG. 16A.
Figure 17A:
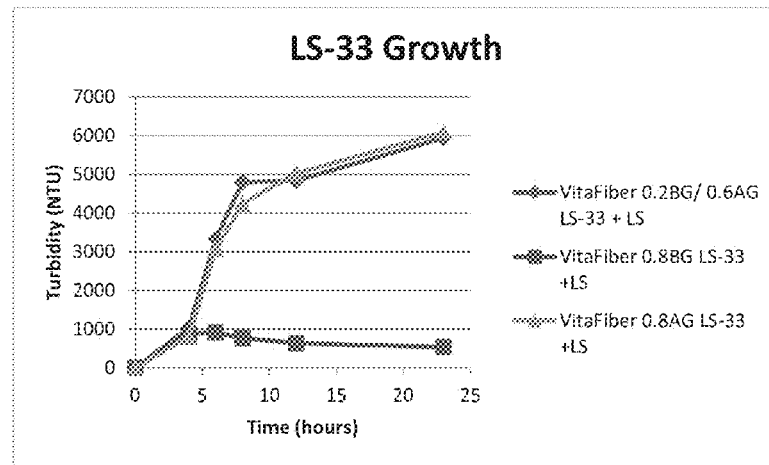
FIG. 17A shows the growth of Latobacillus *salivarius* (LS-33) where VitaFiber™ was pre-digested with one of: (i) α-galatosidase; (ii) β-glucanase; and (iii) a 1:3 blend of β-glucanase and α-galatosidase; before adding LactoStim™ and the other ingredients in No-G-Broth but not polysorbate 80.
Figure 17B:
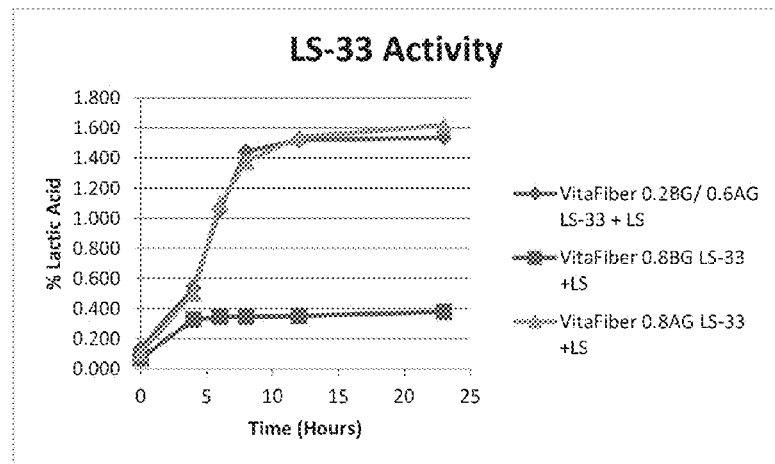
FIG. 17B shows the activity of Latobacillus *salivarius* (LS-33) in the same conditions and media as in FIG. 17A.
Figure 18A:
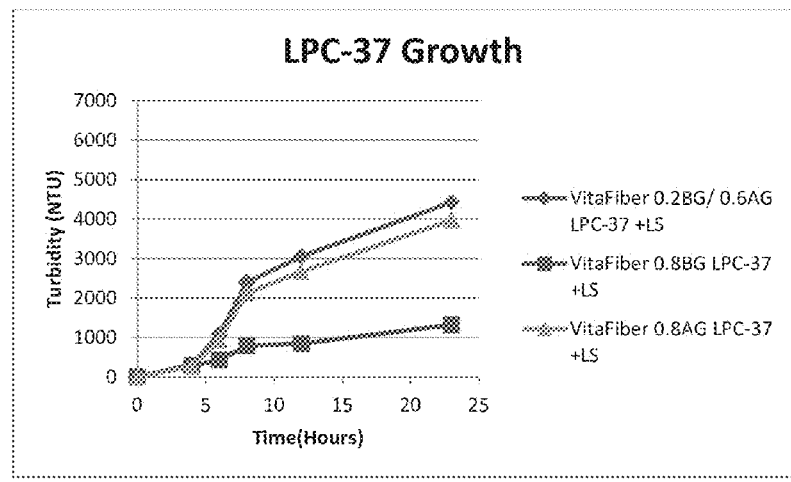
FIG. 18A shows the growth of *Lactobacillus paracasei* (LPC-37) where VitaFiber™ was pre-digested with one of: (i) α-galatosidase; (ii) β-glucanase; and (iii) a 1:3 blend of β-glucanase and α-galatosidase, before adding LactoStim™ and the other ingredients in No-G-Broth but not polysorbate 80.
Figure 18B:
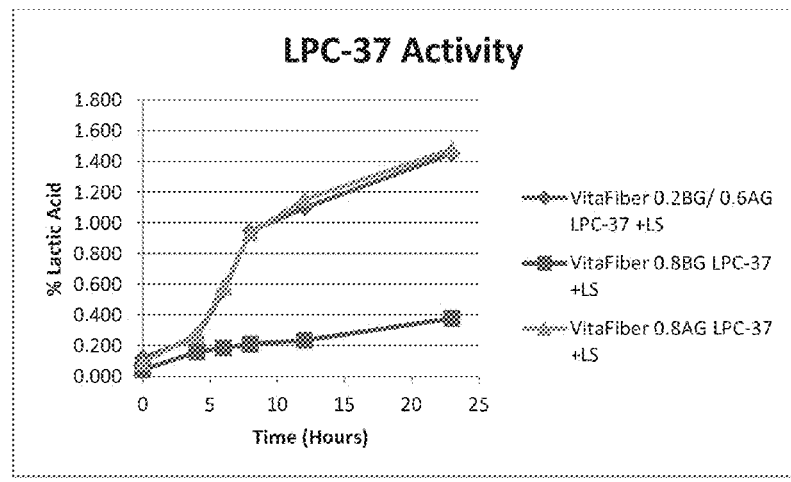
FIG. 18B shows the activity of *Lactobacillus paracasei* (LPC-37) in the same conditions and media as in FIG. 18A.
Figure 19A:
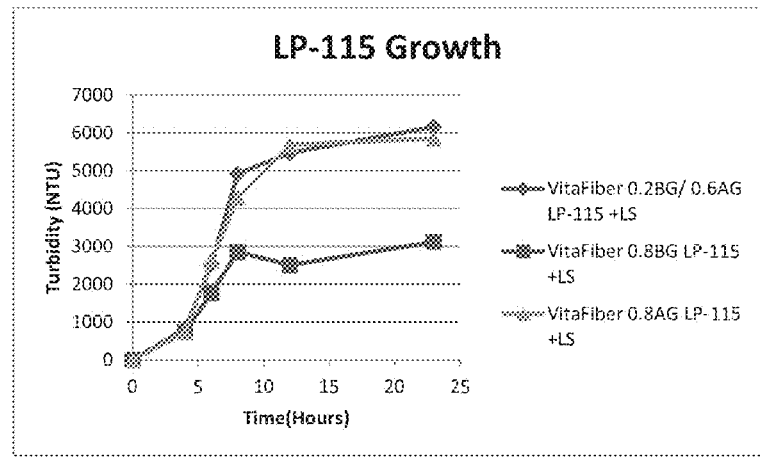
FIG. 19A shows the growth of *Lactobacillus plantarum* (LP-115) where VitaFiber™ was pre-digested with one of: (i) α-galatosidase; (ii) β-glucanase; and (iii) a 1:3 blend of β-glucanase and α-galatosidase before adding LactoStim™ and the other ingredients in No-G-Broth but not polysorbate 80.
Figure 19B:
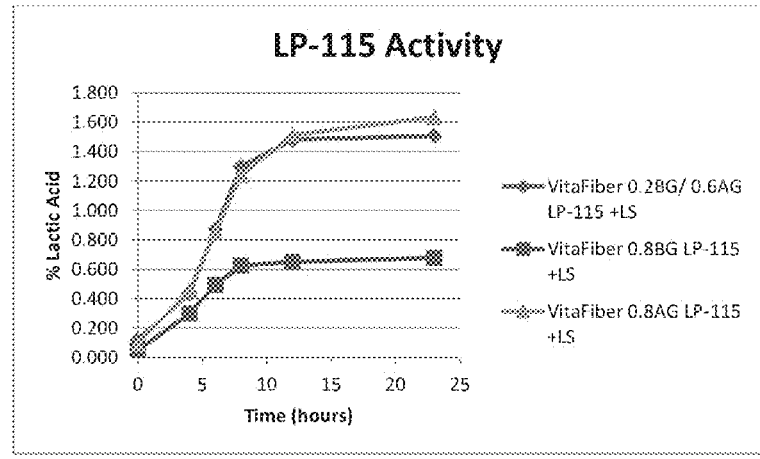
FIG. 19B shows the activity of *Lactobacillus plantarum* (LP-115) in the same conditions and media as in FIG. 19A.
Figure 20A:
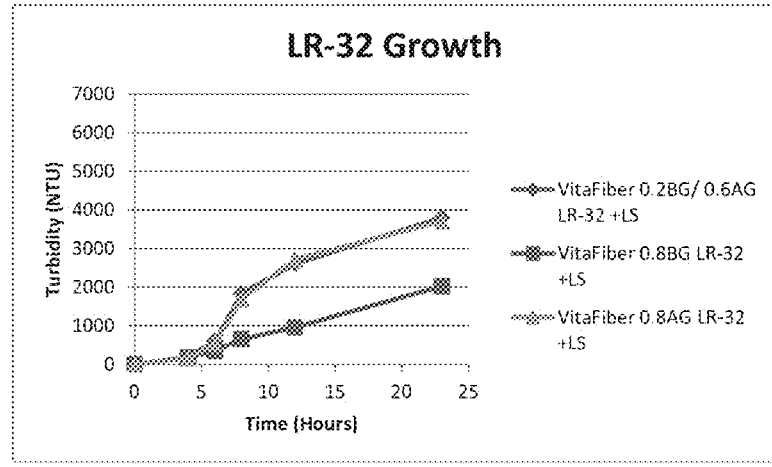
FIG. 20A shows the growth of *Lactobacillus rhamnosus* (Lr-32) where VitaFiber™ was pre-digested with one of: (i) α-galatosidase; (ii) β-glucanase; and (iii) a 1:3 blend of β-glucanase and α-galatosidase before adding LactoStim™ and the other ingredients in No-G-Broth but not polysorbate 80.
Figure 20B:
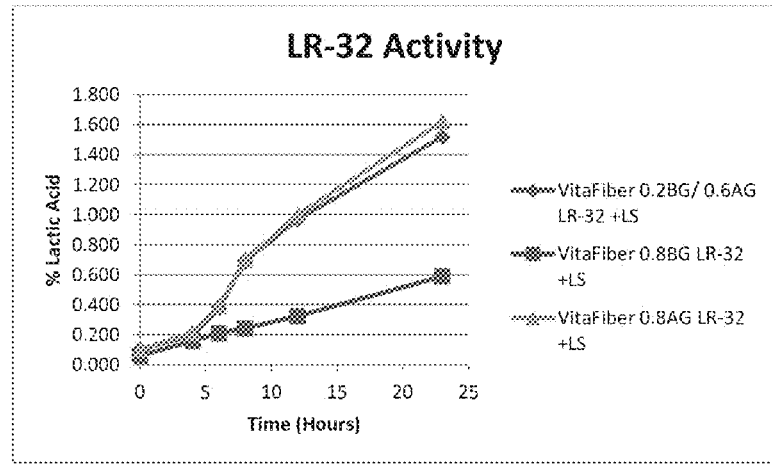
FIG. 20B shows the activity of *Lactobacillus rhamnosus* (Lr-32) in the same conditions and media as in FIG. 20A.
Figure 21A:
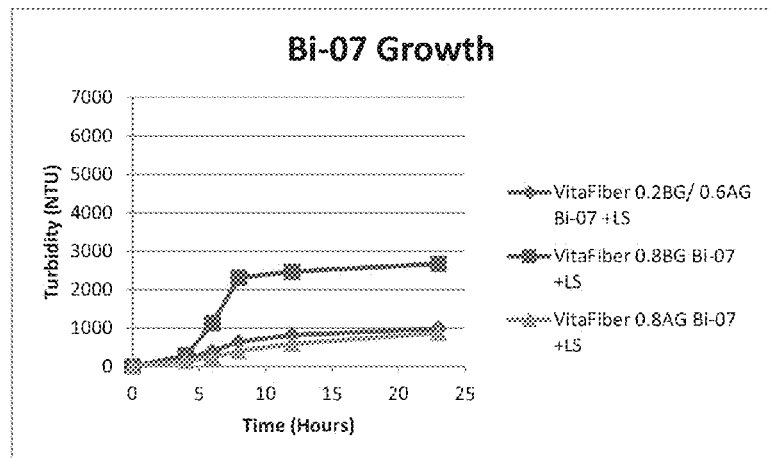
FIG. 21A shows the growth of *Bifidobacterium lactis* (Bi-07) where VitaFiber™ was pre-digested with one of: (i) α-galatosidase; (ii) β-glucanase; and (iii) a 1:3 blend of β-glucanase and α-galatosidase, before adding LactoStim™ and the other ingredients in No-G-Broth but not polysorbate 80.
Figure 21B:
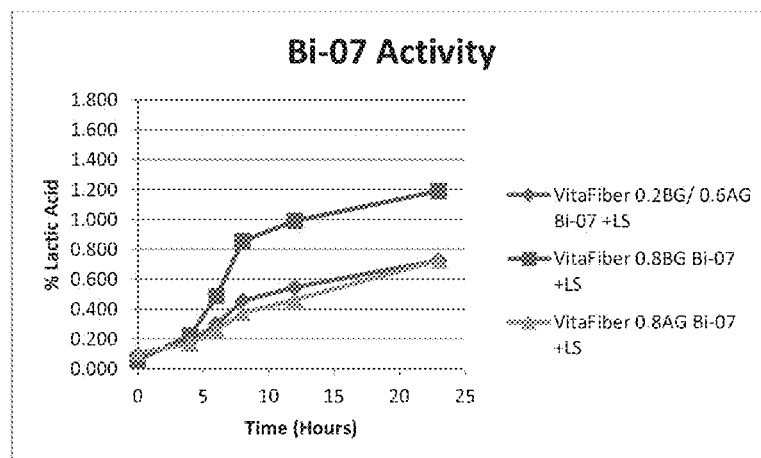
FIG. 21B shows the activity of *Bifidobacterium lactis* (Bi-07) in the same conditions and media as in FIG. 21A.

VitaFiber™ was digested with β-glucanase plus α-galactosidase at either 3:1 or 1:3 (wt:wt) ratios, both with and without subsequent addition of LactoStim™. Each flask was inoculated with 0.14 gram of a 50:50 mix (wt:wt) of BL-04 plus NCFM. The highest activity occurred when VF was digested with 1:3 (wt:wt) β-glucanase/α-galactosidase at 0.2% (wt/vol) followed by adding 0.1% (wt/vol) LactoStim™. This resulted in an activity of 1.512% lactic acid (FIG. 16B). This activity is higher than either of the highest digested VF tests assayed with a single bacterial strain of *Bifidobacterium lactis* or *Lactobacillus acidophilus*.

EXAMPLE#10

The 1:3 ratio of β-glucanase/α-galactosidase (wt:wt) at 0.2% (wt/vol) was also tested with strains of *Lactobacillus salivarius* (LS-33), *Lactobacillus paracasei* (LPC-37), *Lactobacillus plantarum* (LP-115), *Lactobacillus rhamnosus* (Lr-32), and *Bifidobacterium lactis* (Bi-07 strain). As noted with previous experiments, *Lactobacillus* strains had a higher activity when VitaFiber™ was digested with α-galactosidase rather than β-glucanase, and *Bifidobacterium* strains had a higher activity when VF was digested with β-glucanase rather than α-galactosidase. For LS-33, LPC-37, LP-115 and Lr-32, digestion with 0.2% (wt/vol) α-galactosidase had a slightly higher activity than with the 1:3 (wt:wt) β-glucanase/α-galactosidase blend at 0.2% (wt/vol). (FIGS. 17B, 18B, 19B, 20B and 21B).

EXAMPLE#11

Figure 22A:
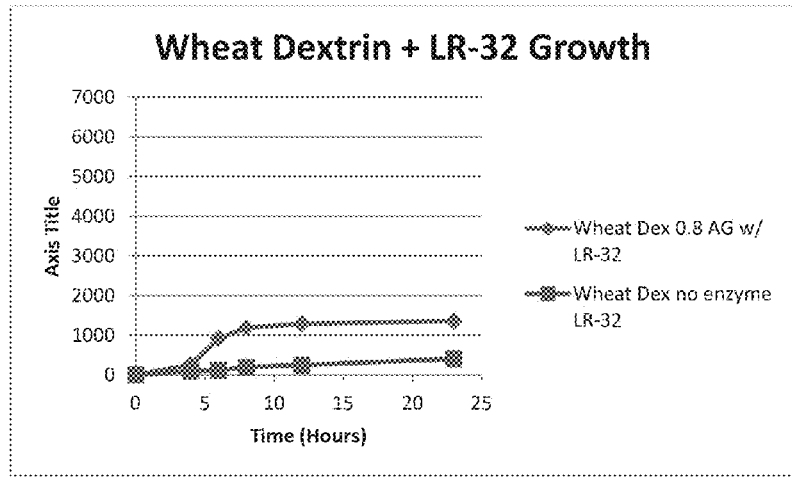
FIG. 22A shows growth of *Lactobacillus rhamnosus* (LR-32) with Wheat Dextrin in No-G-Broth, and where Wheat Dextrin was pre-digested with α-galatosidase before adding the other ingredients in No-G-Broth.
Figure 22B:
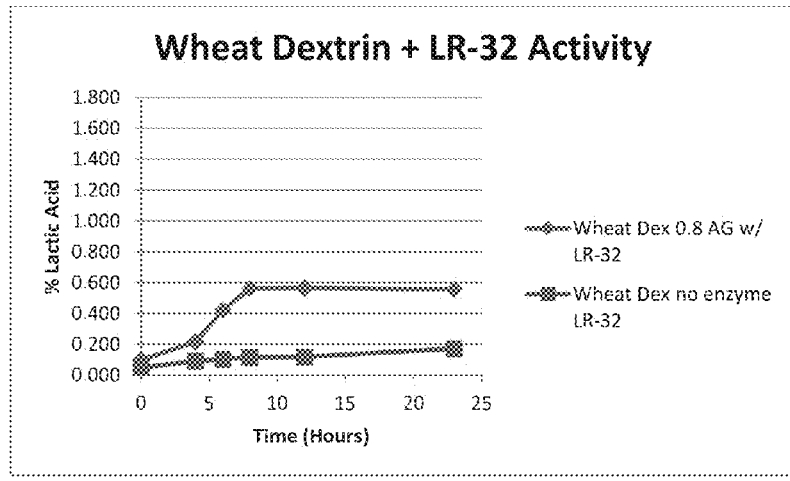
FIG. 22B shows the activity of *Lactobacillus rhamnosus* (LR-32) in the same conditions and media as in FIG. 22A.
Figure 23A:
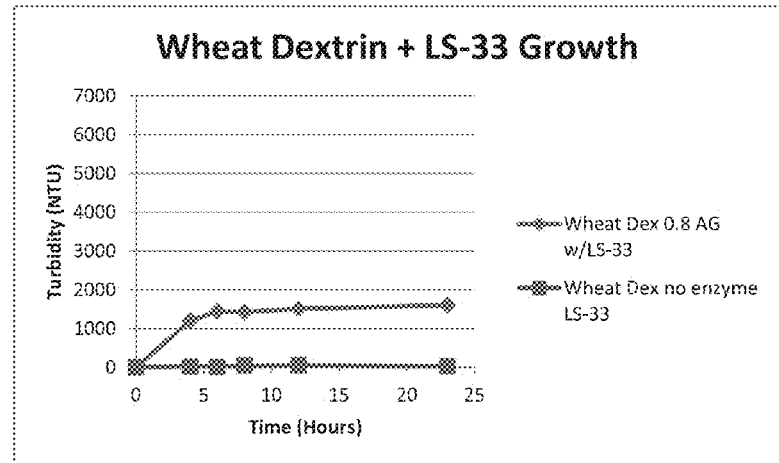
FIG. 23A shows the growth of *Lactobacillus salivarius* (LS-33) with Wheat Dextrin in No-G-Broth, and where Wheat Dextrin was pre-digested with α-galatosidase before adding the other ingredients in No-G-Broth.
Figure 23B:
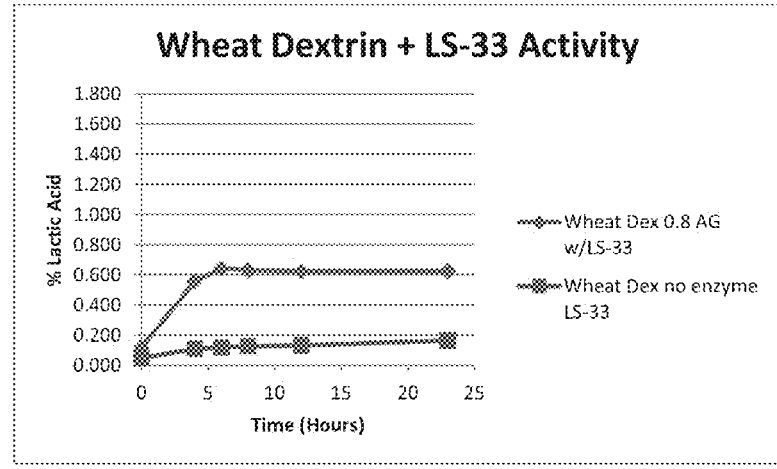
FIG. 23B shows the activity of *Lactobacillus salivarius* (LS-33) in the same conditions and media as in FIG. 23A.
Figure 24A:
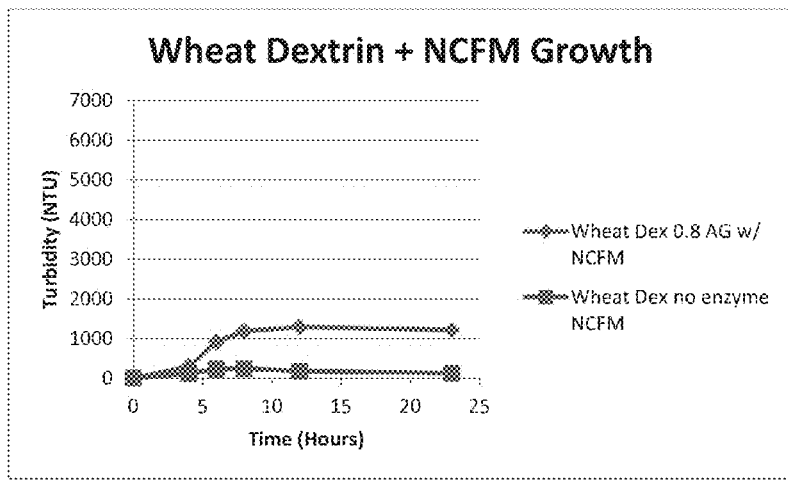
FIG. 24A shows the growth of *Lactobacillus acidophilus* (NCFM) with Wheat Dextrin in No-G-Broth, and where Wheat Dextrin was pre-digested with α-galatosidase before adding the other ingredients in No-G-Broth.
Figure 24B:
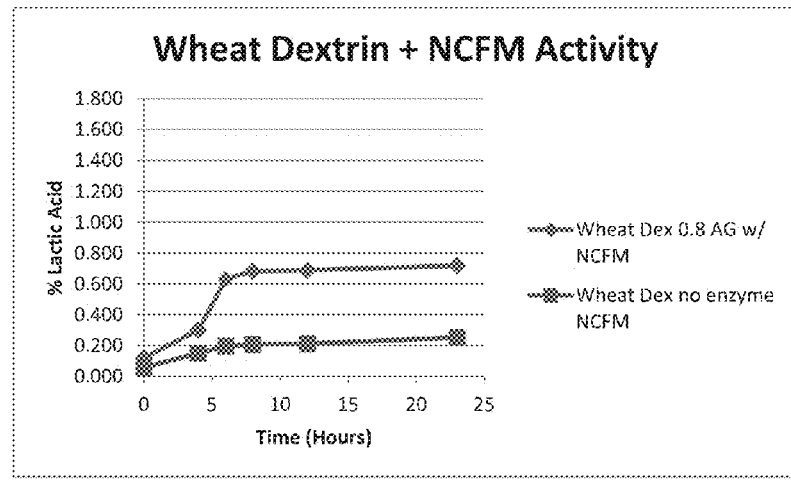
FIG. 24B shows the activity of *Lactobacillus acidophilus* (NCFM) in the same conditions and media as in FIG. 24A.

Growth and activity of *Lactobacillus rhamnosus* (Lr-32), *Lactobacillus salivarius* (LS-33) and *Lactobacillus acidophilus* (NCFM) was tested with wheat dextrin or wheat dextrin digested with α-galactosidase at 0.2% (wt./vol.). (FIGS. 22B; 23B; 24B). In all cases, the digested wheat dextrin generated a higher activity (% lactic acid).

EXAMPLE#12

Figure 25B:
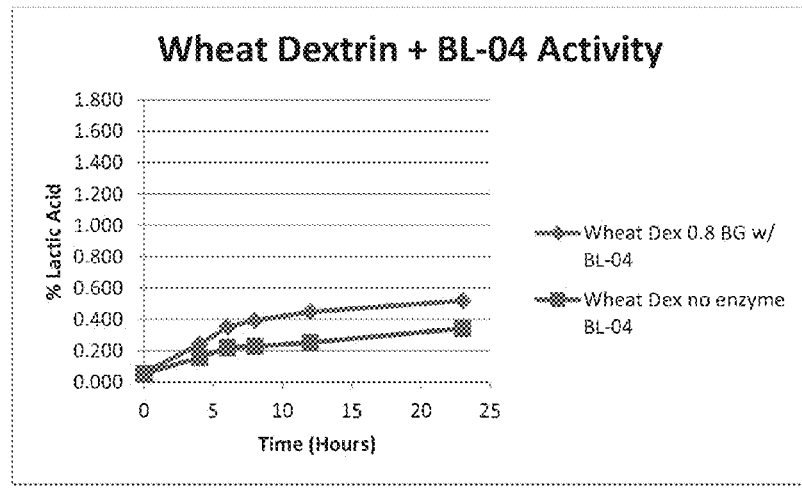
FIG. 25B shows the activity of *Bifidobacterium lactis* (BL-04) in the same conditions and media as in FIG. 25A.
Figure 26A:
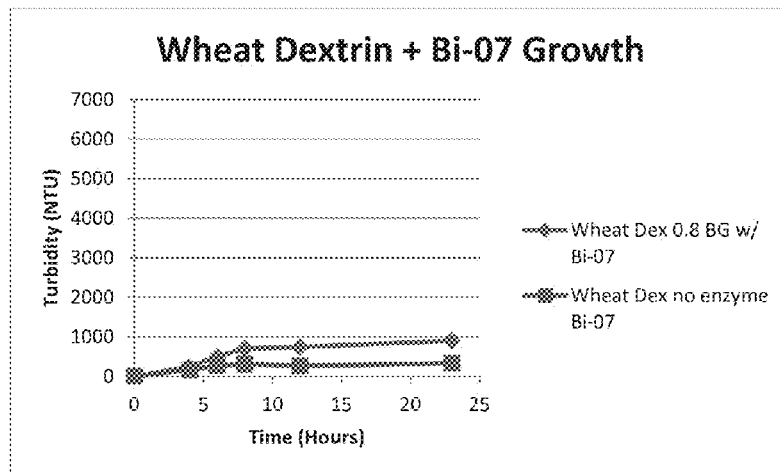
FIG. 26A shows the growth of *Bifidobacterium lactis* (Bi-07) with Wheat Dextrin in No-G-Broth, and where Wheat Dextrin was pre-digested with β-glucanase before adding the other ingredients in No-G-Broth.
Figure 26B:
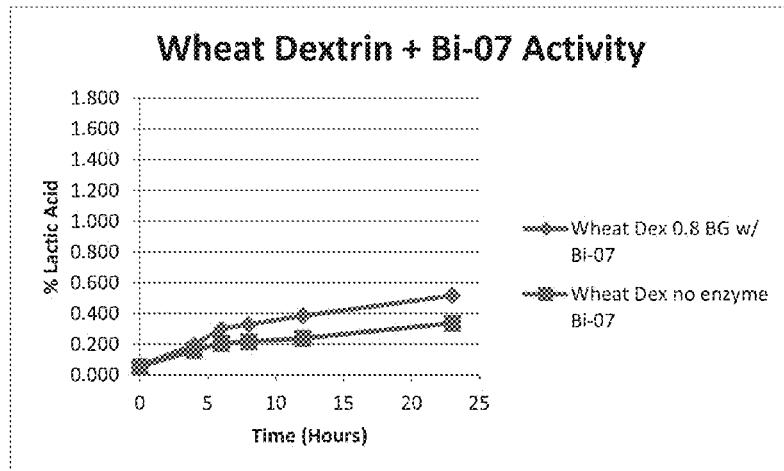
FIG. 26B shows the activity of *Bifidobacterium lactis* (Bi-07) in the same conditions and media as in FIG. 26A.
Figure 27A:
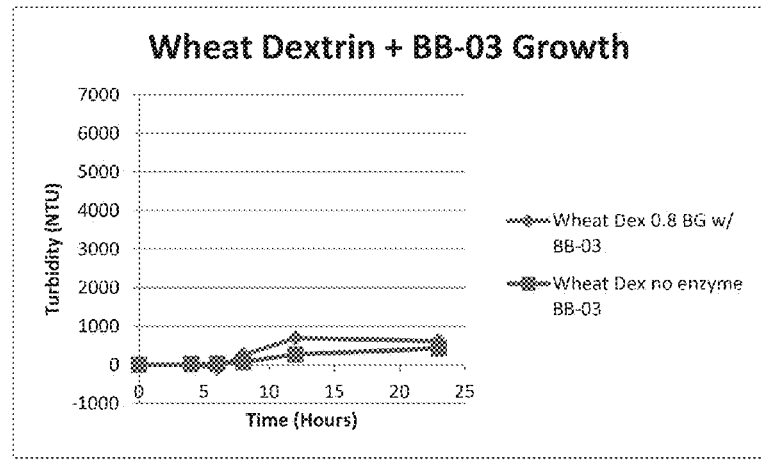
FIG. 27A shows the growth of *Bifidobacterium breve* (BB-03) with Wheat Dextrin in No-G-Broth, and where Wheat Dextrin was pre-digested with β-glucanase before adding the other ingredients in No-G-Broth.
Figure 27B:
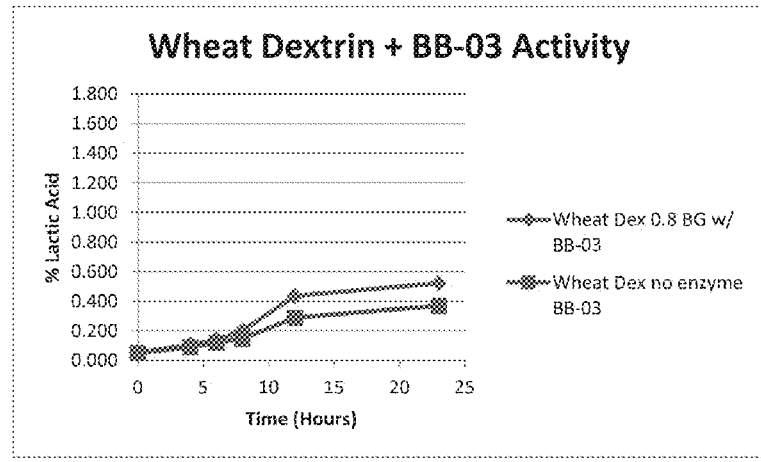
FIG. 27B shows the activity of *Bifidobacterium breve* (BB-03) in the same conditions and media as in FIG. 27A.

Growth and activity of *Bifidobacterium lactis* (BL-04), *Bifidobacterium lactis* (Bi-07) and *Bifidobacterium breve* (BB-03) was tested with wheat dextrin or wheat dextrin digested with β-glucanase at 0.2% (wt/vol). In all cases, the enzyme digested wheat dextrin generated a higher activity (FIGS. 25B, 26B; 27B).

EXAMPLE#13

Growth and activity of *Lactobacillus plantarum* (LP-115) was tested with wheat dextrin or wheat dextrin digested with either 0.2% (wt/vol) α-galactosidase or 0.2% (wt/vol) pectinase. Wheat dextrin digested with 0.2% (wt/vol) α-galactosidase generated a higher activity (FIG. 28B).

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A formulation for enhancing *lactobacillus* growth or activity in vivo comprising *lactobacillus*, α-galactosidase, isomalto-oligosaccharide and fiber-digesting enzymes.

2. The formulation of claim 1 wherein the *lactobacillus* species is *Lactobacillus acidophilus, Lactobacillus salivarius, Lactobacillus paracasei, Lactobacillus plantarum* or *Lactobacillus rhamnosus*.

3. The formulation of claim 1 further including sunflower lecithin and/or oleic acid.

4. The formulation of claim 1 further including polysorbate 80.

5. The formulation of claim 1 wherein the fiber-digesting enzymes are cellulase, hemicellulase, pectinase or xylanase.

6. The formulation of claim 5 wherein the cellulase is cellulase-TL or cellulase-AN.

7. The formulation of claim 1 further including inulin, wheat dextrin, and partially hydrolyzed guar gum.

8. The formulation of claim 1 further including protease enzymes.

9. The formulation of claim 8 wherein the protease enzymes are papain, bromelain, fungal protease, fungal acid-protease, bacterial protease, fungal peptidase, nattokinase, serapeptase, trypsin, chymotrypsin pancreatin or pepsin.

10. The formulation of claim 1 wherein the formulation further includes β-glucanase.

11. The formulation of claim 1 wherein the formulation further includes food.

12. The formulation of claim 11 wherein the food is milk products including yogurt.

13. The formulation of claim 1 wherein the formulation further includes carriers, binders or adsorbents.

14. The formulation of claim 13 wherein the carriers, binders or adsorbents are food grade starches or silicates.

15. A formulation for enhancing *lactobacillus* growth or activity in vivo comprising *lactobacillus*, α-galactosidase, β-glucanase and isomalto-oligosaccharide.

16. The formulation of claim 15 further including fiber-digesting enzymes.

17. The formulation of claim 15 wherein the *lactobacillus* species is *Lactobacillus acidophilus, Lactobacillus salivarius, Lactobacillus paracasei, Lactobacillus plantarum* or *Lactobacillus rhamnosus*.

18. The formulation of claim 15 further including sunflower lecithin and/or oleic acid.

19. The formulation of claim 15 further including polysorbate 80.

20. The formulation of claim 15 further including fiber-digesting enzymes.

21. The formulation of claim 20 wherein the fiber-digesting enzymes are cellulase, hemicellulase, pectinase or xylanase.

22. The formulation of claim 21 wherein the cellulase is cellulase-TL or cellulase-AN.

23. The formulation of claim 15 further including inulin, wheat dextrin, and partially hydrolyzed guar gum.

24. The formulation of claim 15 further including protease enzymes.

25. The formulation of claim 24 wherein the protease enzymes are papain, bromelain, fungal protease, fungal acid-protease, bacterial protease, fungal peptidase, nattokinase, serapeptase, trypsin, chymotrypsin pancreatin or pepsin.

26. The formulation of claim 15 wherein the formulation further includes food.

27. The formulation of claim 26 wherein the food is milk products including yogurt.

28. The formulation of claim 15 wherein the formulation further includes carriers, binders or adsorbents.

29. The formulation of claim 28 wherein the carriers, binders or adsorbents are food grade starches or silicates.

* * * * *